United States Patent
Assia et al.

(10) Patent No.: US 9,788,824 B2
(45) Date of Patent: *Oct. 17, 2017

(54) IRIS RETRACTION METHOD

(71) Applicant: APX OPHTHALMOLOGY LTD., Haifa (IL)

(72) Inventors: Ehud Assia, Tel Aviv (IL); Eliahu Eliachar, Haifa (IL); Nir Lilach, Kfar Yehoshua (IL)

(73) Assignee: APX OPTHALMOLOGY LTD., Haifa (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/477,558

(22) Filed: Apr. 3, 2017

(65) Prior Publication Data

US 2017/0202549 A1   Jul. 20, 2017

Related U.S. Application Data

(63) Continuation of application No. 14/488,393, filed on Sep. 17, 2014, now Pat. No. 9,610,072, which is a continuation-in-part of application No. 13/505,510, filed as application No. PCT/US2010/055026 on Nov. 2, 2010, now abandoned.

(60) Provisional application No. 61/257,087, filed on Nov. 2, 2009.

(51) Int. Cl.
  *A61B 17/02*   (2006.01)
(52) U.S. Cl.
  CPC ................. *A61B 17/0231* (2013.01)
(58) Field of Classification Search
  CPC ... A61B 17/02; A61B 17/0218; A61B 17/025; A61B 17/0231; A61B 2017/0225; A61B 2017/0287

USPC ........................ 600/201–246; 81/485; 294/97
See application file for complete search history.

(56) References Cited

U.S. PATENT DOCUMENTS

| | | | | |
|---|---|---|---|---|
| 2,075,534 A | * | 3/1937 | McCormack | A61B 1/24 600/219 |
| 2,234,715 A | * | 3/1941 | Whitney | A01N 1/00 27/21.1 |
| 2,238,563 A | * | 4/1941 | Jacques | A61B 17/02 27/21.1 |

(Continued)

FOREIGN PATENT DOCUMENTS

| EP | 0769271 A1 | 4/1997 |
|---|---|---|
| EP | 1029508 A1 | 8/2000 |

(Continued)

OTHER PUBLICATIONS

PCT Written Opinion of the International Searching Authority for PCT/2010/055026, mailed May 2, 2012 (7 pages).

*Primary Examiner* — Eric S Gibson
(74) *Attorney, Agent, or Firm* — Roach Brown McCarthy & Gruber P.C.; Kevin D. McCarthy

(57) ABSTRACT

An iris retractor made of two slender elements operatively coupled via a joining mechanism, wherein each slender element has an iris grabbing hook located at its distal end; and a handle located at the proximal end of the slender element, wherein the joining mechanism is configured to endow the iris retractor with at least two configurations: a retracted configuration and an expanded configuration, wherein the length of each slender element is between 4 mm to 14 mm.

8 Claims, 26 Drawing Sheets

(56) References Cited

U.S. PATENT DOCUMENTS

| | | | | |
|---|---|---|---|---|
| 3,316,913 A * | 5/1967 | Swenson | A61M 16/0488 | 604/28 |
| 3,616,497 A * | 11/1971 | Esposito | H01L 23/291 | 24/542 |
| 3,742,560 A * | 7/1973 | Kessler | A61B 1/24 | 600/218 |
| 3,916,907 A * | 11/1975 | Peterson | A61B 17/025 | 29/239 |
| 4,037,589 A * | 7/1977 | McReynolds | A61B 17/0231 | 600/209 |
| 4,257,406 A * | 3/1981 | Schenk | A61B 17/0231 | 600/219 |
| 4,321,916 A * | 3/1982 | McKee | A61F 9/007 | 600/209 |
| 4,386,608 A * | 6/1983 | Ehrlich | A61F 9/0026 | 604/150 |
| 4,991,567 A * | 2/1991 | McCuen, II | A61B 17/0231 | 600/204 |
| 5,030,224 A * | 7/1991 | Wright | A61B 17/083 | 600/209 |
| 5,054,906 A * | 10/1991 | Lyons, Jr. | A61B 3/0008 | 351/205 |
| 5,171,254 A * | 12/1992 | Sher | A61B 17/0231 | 600/232 |
| 5,174,279 A * | 12/1992 | Cobo | A61F 9/007 | 600/206 |
| 5,176,129 A * | 1/1993 | Smith | A61B 17/0206 | 600/217 |
| 5,290,292 A * | 3/1994 | Householder | A61B 17/0231 | 600/209 |
| 5,292,324 A * | 3/1994 | McDonald | A61F 9/00709 | 606/107 |
| 5,341,798 A * | 8/1994 | Grounauer | A61B 17/0231 | 600/236 |
| 5,441,040 A * | 8/1995 | Williams, Jr. | A61B 17/0231 | 600/236 |
| 5,484,447 A * | 1/1996 | Waldock | A61B 17/0231 | 33/511 |
| 5,556,417 A * | 9/1996 | Sher | A61B 17/0231 | 600/236 |
| 5,591,203 A * | 1/1997 | Fahy | A61B 17/11 | 433/159 |
| 5,607,446 A * | 3/1997 | Beehler | A61B 17/0218 | 600/206 |
| 5,618,261 A * | 4/1997 | Nevyas | A61B 17/0231 | 600/236 |
| 5,620,458 A * | 4/1997 | Green | A61B 17/0218 | 600/214 |
| 5,662,659 A * | 9/1997 | McDonald | A61F 9/00709 | 606/107 |
| 5,716,328 A * | 2/1998 | Grieshaber | A61B 17/0231 | 600/206 |
| 5,772,582 A * | 6/1998 | Huttner | A61B 1/233 | 600/219 |
| 5,807,244 A * | 9/1998 | Barot | A61B 17/0231 | 600/236 |
| 5,993,384 A * | 11/1999 | Lunsford | A61B 1/313 | 600/209 |
| 6,183,480 B1 * | 2/2001 | Mackool | A61B 17/0231 | 606/107 |
| 6,261,296 B1 * | 7/2001 | Aebi | A61B 17/025 | 600/219 |
| 6,283,913 B1 * | 9/2001 | Seibel | A61B 1/32 | 600/219 |
| 6,299,617 B1 * | 10/2001 | Stamler | A61B 17/0231 | 600/236 |
| 6,302,842 B1 * | 10/2001 | Auerbach | A61B 17/0206 | 600/219 |
| 6,309,349 B1 * | 10/2001 | Bertolero | A61B 17/0206 | 600/210 |
| 6,332,866 B1 * | 12/2001 | Grieshaber | A61B 17/0231 | 600/210 |
| 6,425,901 B1 * | 7/2002 | Zhu | A61B 17/0057 | 600/208 |
| 6,440,065 B1 * | 8/2002 | Hered | A61B 1/32 | 600/236 |
| 6,544,169 B2 * | 4/2003 | Putrino | A61B 17/0231 | 600/210 |
| 6,561,974 B1 * | 5/2003 | Grieshaber | A61B 17/0231 | 600/206 |
| 6,675,805 B1 * | 1/2004 | Graether | A61B 17/0231 | 128/849 |
| 6,702,739 B2 * | 3/2004 | Levisman | A61B 1/24 | 600/217 |
| 6,746,471 B2 * | 6/2004 | Mortier | A61B 17/00234 | 600/201 |
| 7,175,594 B2 * | 2/2007 | Foulkes | A61B 1/00094 | 600/219 |
| 7,666,190 B2 * | 2/2010 | Tano | A61F 2/1662 | 600/236 |
| D624,648 S * | 9/2010 | Terry | D24/135 | |
| D631,157 S * | 1/2011 | Terry | D24/135 | |
| D639,942 S * | 6/2011 | Terry | D24/135 | |
| 7,985,180 B2 * | 7/2011 | Brown | A61B 1/32 | 600/235 |
| 8,025,668 B2 * | 9/2011 | McCartney | A61B 8/0841 | 600/122 |
| 8,083,751 B2 * | 12/2011 | Olsen | A61B 17/0231 | 600/236 |
| D663,416 S * | 7/2012 | Terry | D24/135 | |
| 8,257,256 B1 * | 9/2012 | Krolman | A61B 17/0231 | 600/236 |
| 8,267,970 B2 * | 9/2012 | Serhan | A61B 17/7071 | 600/236 |
| 8,311,624 B2 * | 11/2012 | Singh | A61B 17/0231 | 604/20 |
| 8,323,296 B2 | 12/2012 | Malyugin | | |
| 8,439,833 B2 * | 5/2013 | Christensen | A61B 17/0231 | 600/236 |
| 8,496,583 B1 * | 7/2013 | Reynard | A61B 17/0231 | 600/235 |
| 8,562,522 B2 * | 10/2013 | Antanaitis | A61B 17/0206 | 600/225 |
| 2002/0062065 A1 * | 5/2002 | Daniel | A61B 17/00234 | 600/235 |
| 2003/0055319 A1 * | 3/2003 | Chang | A61B 17/0206 | 600/210 |
| 2003/0055320 A1 * | 3/2003 | McBride | A61B 17/0206 | 600/217 |
| 2004/0225196 A1 * | 11/2004 | Ruane | A61B 1/32 | 600/220 |
| 2005/0215864 A1 * | 9/2005 | Jang | A61B 17/0206 | 600/217 |
| 2005/0267336 A1 * | 12/2005 | Bertolero | A61B 1/32 | 600/219 |
| 2006/0269888 A1 | 11/2006 | Ogawa | | |
| 2007/0244516 A1 * | 10/2007 | Chiu | A61B 17/28 | 606/207 |
| 2007/0299315 A1 * | 12/2007 | Geller | A61B 17/0206 | 600/217 |
| 2008/0015416 A1 * | 1/2008 | Rucker | A61B 17/0218 | 600/210 |
| 2008/0021286 A1 * | 1/2008 | Risto | A61B 17/02 | 600/219 |
| 2008/0077171 A1 * | 3/2008 | Blain | A61B 17/0206 | 606/190 |
| 2008/0172085 A1 * | 7/2008 | Chiu | A61B 17/0482 | 606/205 |
| 2008/0188860 A1 * | 8/2008 | Vold | A61F 9/00736 | 606/107 |
| 2008/0234765 A1 * | 9/2008 | Frasier | A61B 17/7086 | 606/86 A |
| 2008/0243139 A1 * | 10/2008 | Dusek | A61B 17/0231 | 606/107 |
| 2009/0187080 A1 * | 7/2009 | Seex | A61B 17/02 | 600/210 |
| 2009/0227846 A1 * | 9/2009 | Beck | A61B 1/32 | 600/236 |

(56) References Cited

U.S. PATENT DOCUMENTS

| | | | |
|---|---|---|---|
| 2010/0076270 A1* | 3/2010 | Merriam | A61B 17/0231 600/235 |
| 2010/0331878 A1* | 12/2010 | Kleinwachter | A61B 17/02 606/205 |
| 2011/0060194 A1* | 3/2011 | Risto | A61B 1/32 600/210 |
| 2011/0077468 A1* | 3/2011 | Finger | A61B 1/32 600/236 |
| 2011/0098538 A1* | 4/2011 | Terry | A61B 17/0231 600/236 |
| 2011/0105848 A1* | 5/2011 | Sadovsky | A61B 17/0218 600/204 |
| 2011/0275903 A1* | 11/2011 | Shelton | A61B 17/0231 600/236 |
| 2012/0232351 A1* | 9/2012 | Assia | A61B 17/0231 600/217 |
| 2012/0289786 A1* | 11/2012 | Dusek | A61B 17/0231 600/236 |
| 2013/0072760 A1* | 3/2013 | Terry | A61B 17/0231 600/236 |
| 2013/0123581 A1* | 5/2013 | Fritzinger | A61B 1/32 600/201 |
| 2013/0131458 A1* | 5/2013 | Malyugin | A61B 1/32 600/236 |
| 2014/0288380 A1* | 9/2014 | Assia | A61B 17/0231 600/236 |
| 2015/0065809 A1* | 3/2015 | Assia | A61B 17/0231 600/217 |
| 2015/0359529 A1* | 12/2015 | Ganiban | A61B 17/0231 600/203 |

FOREIGN PATENT DOCUMENTS

| | | | |
|---|---|---|---|
| EP | 1161925 A1 | 12/2001 | |
| NO | 2008/115455 A1 | 9/2008 | |
| NO | 2013062983 A2 | 5/2013 | |
| WO | WO 2007068128 A1 * | 6/2007 | A61B 17/0206 |
| WO | WO 2009022887 A2 * | 2/2009 | A61B 17/0206 |

\* cited by examiner

IRIS RETRACTION METHOD

CROSS-REFERENCE TO RELATED APPLICATIONS

This application is a continuation of U.S. patent application Ser. No. 14/488,393, filed Sep. 17, 2014, which is a continuation-in-part of U.S. patent application Ser. No. 13/505,510, filed May 2, 2012, which is a national phase application of PCT Patent Application No. PCT/US2010/055026, filed Nov. 2, 2010, which claims priority to U.S. Provisional Patent Application No. 61/257,087, filed Nov. 2, 2009. These applications are incorporated herein by reference in their entirety.

FIELD OF THE INVENTION

The present invention relates generally to an iris retractor used in ophthalmic surgical procedures.

BACKGROUND OF THE INVENTION

A retractor is a surgical instrument by which a surgeon can either actively separate the edges of a surgical incision or wound, or can hold back underlying organs and tissues, so that body parts under the incision are accessed.

The term retractor is also used to describe the distinct, hand-cranked devices such as rib spreaders (also known as thoracic retractors, or distractors) with which surgeons may forcefully drive tissues apart to obtain the exposure. For specialized situations such as spinal surgery retractors have been fitted both with suction and with fiberoptic lights to keep a surgical wound dry and illuminated.

Retractors are available in many shapes, sizes, and styles. The general term retractor usually describes a simple handheld steel tool possessing a curved, hooked, or angled blade fitted with a comfortable handle, that when in place maintains the desired position of a given region of tissue.

There are various ophthalmic procedures that require the dilation of the pupil. For example, a lens with a cataract is typically removed from the eye by phacoemulsification. This procedure breaks up the lens typically with an ultrasonically driven tool. The tool has an aspiration port that aspirates the broken lens material from the patient's ocular-chamber. It is desirable to expand the pupil during phacoemulsification to provide the surgeon with a wide view of the lens. One technique for expanding the pupil includes pulling back or retracting the iris with what is referred to as an iris retractor, and holding the iris at its outer edges.

SUMMARY OF THE INVENTION

The present invention seeks to provide an improved iris retractor, as described in more detail hereinbelow.

There is thus provided in accordance with an embodiment of the present invention an iris retractor including a plurality of iris grabbing hooks disposed or formed at a distal end of slender elements, and a proximal handle at a proximal end of the slender elements, the slender elements resiliently moving between retracted and expanded positions by manipulation of the slender elements, wherein in the retracted position, the hooks are close to one another and the slender elements are close to one another, and wherein in the expanded position, the hooks are separate and spaced apart from each other and distal portions of the slender elements are separate and spaced apart from each other.

In accordance with an embodiment of the present invention a retaining element retains the slender elements in the expanded position until the handle (located at the proximal portion or proximal end of a device such as described herein) is manipulated to move the slender elements to the retracted position. In accordance with an embodiment of the present invention a retaining element retains the slender elements in the retracted position until the handle is manipulated to allow the slender elements to move to the expanded position. In some of the embodiments, the retaining element comprises a spring.

In accordance with another embodiment of the present invention a portion of the retaining element is coupled to the slender element within a groove formed in proximity to a handle. In another embodiment, the handle is received in the groove. In another embodiment, a first end of the retaining element is coupled to a first slender element within a groove formed in proximity to a handle and a second end of the retaining element is coupled to a second slender element within a groove formed in proximity to a handle. In another embodiment, the handle is received in the groove.

In accordance with an embodiment of the present invention, a retractor includes: a first slender element and a second slender element operatively coupled via a joining mechanism, wherein the first slender element and the second slender element comprise: a grabbing hook located at the distal portion of the first slender element and the second slender element; and a handle located at the proximal portion of the first slender element and the proximal portion of the second slender element, wherein the joining mechanism is configured to endow the iris retractor with at least two configuration: a retracted configuration and an expanded configuration, wherein the length of the first slender element and the second slender element is between 4 mm to 15 mm.

In accordance with an embodiment of the present invention, a kit is provided, wherein the kit comprises a pair of retractors of the invention and possibly an instruction manual.

Additionally, a method for dilating a pupil in a subject in need thereof, is provided herein. The method comprising: performing two opposing 0.5 to 4 mm long incisions in the cornea; inserting through each one of the incisions an iris retractor in a fully retracted configuration; positioning the distal end of the iris retractor behind the iris; expanding the iris retractor; wherein the iris retractor comprises: two slender elements operatively coupled via a joining mechanism, wherein each slender element comprises: an iris grabbing hook located at the distal portion of the slender element; and a handle located at the proximal portion of the slender element, wherein the joining mechanism is configured to endow said iris retractor with at least two configuration: a retracted configuration and an expanded configuration, wherein the length of each slender element is between 4 mm to 15 mm.

In accordance with still another embodiment of the present invention the slender elements are pivotally attached to one another at a pivot.

In accordance with an embodiment of the present invention a tip of the slender element includes a U-shaped hook with a short distal extension.

In accordance with an embodiment of the present invention a tip of the slender element extends from a proximal sleeve.

There is also provided in accordance with an embodiment of the present invention a method for retraction of an iris including providing an iris retractor that includes a plurality of hooks disposed or formed at a distal end of slender elements, and a proximal handle at a proximal end of the slender elements, the slender elements resiliently moving between retracted and expanded positions by manipulation of the handle, wherein in the retracted position, the hooks are close to one another and the slender elements are close to one another, and wherein in the expanded position, the hooks are separate and spaced apart from each other and the distal portions of the slender elements are separate and spaced apart from each other, inserting the slender elements in the retracted position through a small incision near a Limbus of an eye, manipulating the handle to move the slender elements to the expanded position, and grasping and retracting a portion of the iris with the hooks.

Two or more incisions each for inserting slender elements can be made at a different position than an incision for phacoemulsification.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1A:
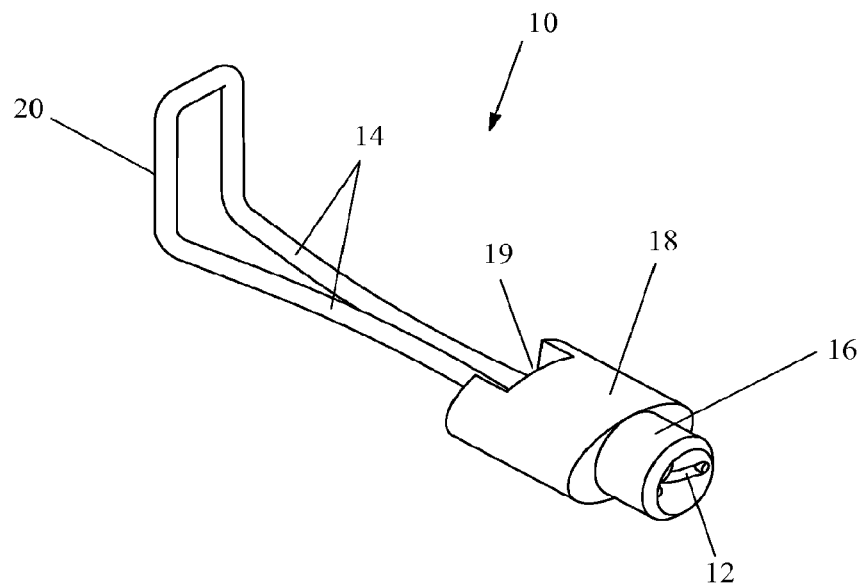
FIGS. 1A-1C are simplified perspective, top-view and side-view illustrations, respectively, of an iris retractor, in a non-expanded orientation, constructed and operative in accordance with an embodiment of the present invention.
Figure 1B:
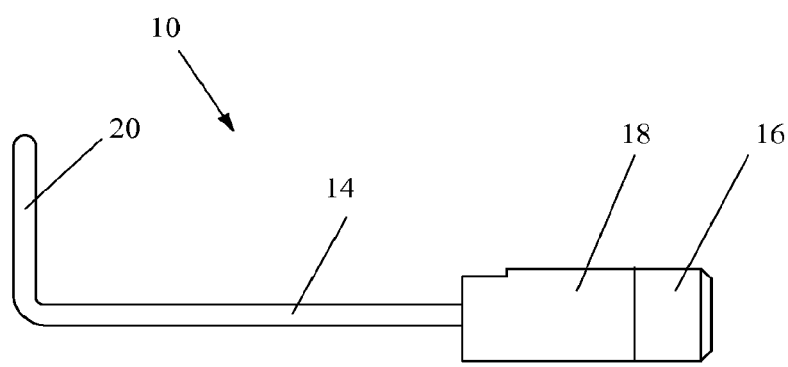
Figure 1C:
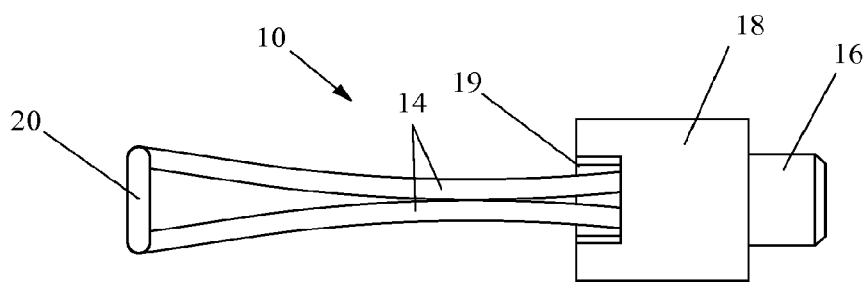

In one embodiment, a retractor of the invention is used for retracting and/or exposing a tissue. In one embodiment, a retractor of the invention is used for retracting and/or exposing a tissue within the eye. In one embodiment, an iris retractor of the invention is used for dilating a pupil.

In some embodiments, the joining mechanism is the spring. In some embodiments, such as but not limited to FIGS. 1-3—pre shaped arms are formed from one elastic rod—element 20 join's and position's the two arms, In some embodiments, the arms (slender elements) expand when extended through element 18 due to their prior designed shape, this embodiment expanded or retracted state is self held according to the longitudinal position of the arms in element 18. In some embodiments, such as but not limited to FIGS. 4-5 one elastic rod (such as element 40)—spring expands the arms. In some embodiments, retraction is achieved by applying squeezing at elements 37 or at the proximal handles (decreasing the distance between the handles) thus closing the retractor. In some embodiments, such as but not limited to FIGS. 6-7: a pivot joins the slender elements; spring (such as 60) keeps the slender elements in an expanded orientation. In some embodiments, such as but not limited to FIGS. 4, 5 and 9: the retractor is one piece shaped retractor.

In some embodiment, a pivot such as in FIGS. 6, 7, 10, 11 and 14 joins the two slender elements. In some embodiment, a pivot and a spring such as in FIGS. 6, 7, 10, 11 and 14 joins the two slender elements. In some embodiment, at least a portion of a spring in the most proximal of a retractor as described herein. In some embodiments, a spring is a coil spring. In some embodiments, a spring is a metal spring (such as 200/208/701). In some embodiments, the slender elements are elastic and/or deformable. In some embodiments, the spring is elastic and/or deformable.

In one embodiment, provided herein an iris retractor comprising: two slender elements operatively coupled via a joining mechanism, wherein each slender element (arm) comprises: (1) an iris grabbing hook located at the distal portion or distal end of the slender element (also referred to as "distal hook"); and (2) a handle located at the proximal portion or proximal end of the slender element (also referred to as "proximal handle"), wherein the joining mechanism is configured to endow the iris retractor with at least two configuration: a retracted configuration and an expanded configuration, wherein the length of each slender element is between 2 mm to 18 mm. In one embodiment, each slender element comprises one distal hook and one proximal handle.

In some embodiments, the handle is a portion of the slender element. In some embodiments, the handle defines the proximal end of a slender element. In some embodiments, the handle is adapted to maintain or anchor a spring element. In some embodiments, a handle has a round shape with a groove and/or opening (such as in FIG. 14). In some embodiments, the groove is a rounded groove. In some embodiments, the opening is connected to the groove 0.7 mm or less. In some embodiments, the opening is 0.5 mm or less. In some embodiments, the opening is 0.15 mm or less. In some embodiments, the opening is 0.4 mm or less. In some embodiments, the opening is an insertion spot for a spring element. In some embodiments, each one of the round proximal end-handle is ear shaped. In some embodiments, each one of the round proximal ends-handles anchors one end of the spring element. In some embodiments, the handle is a groove with an opening wherein the groove anchors one end of the spring. In some embodiments, the proximal end of the retractor is the spring.

In some embodiments, the length of each slender element is between 3 mm to 16 mm. In some embodiments, the length of each slender element is between 5 mm to 15 mm. In some embodiments, the length of each slender element is between 4 mm to 14 mm. In some embodiments, the length of the slender elements with one retractor is the same.

In another embodiment, provided herein an iris retractor comprising: two slender elements coupled via a pivot (such as but not limited to element 705), wherein each slender element (arm) comprises: (1) an iris grabbing hook located at the distal end of the slender element; and (2) a handle located at the proximal end of the slender element, wherein the iris retractor is normally, naturally, and/or by default (no exertion of force) is in an expanded configuration, wherein the length of each slender element is between 4 mm to 15 mm.

In another embodiment, provided herein an iris retractor comprising: two slender elements coupled via a pivot, wherein each slender element (arm) comprises: (1) an iris grabbing hook (such as formed by teeth 703 and 704) located at the distal end of the slender element; and (2) a handle located (such as but not limited to handle 707) at the proximal end of the slender element, wherein a spring coupled to the proximal end or portion of the slender elements maintains the retractor in a an expanded configuration, wherein the length of each slender element is between 4 mm to 15 mm.

Reference is now made to FIGS. 1A-3C, which illustrate an iris retractor 10, constructed and operative in accordance with a non-limiting embodiment of the present invention.

Iris retractor, in some embodiments, includes a grabbing hook ending each slender element at its proximal end (such as element 12 (FIGS. 2A-3C)) disposed or formed at a distal end or portion of one or more slender elements 14. In another embodiment, a grabbing hook protrudes 0.1 mm to 1.5 mm laterally from the lateral surface of the slender element. In another embodiment, a grabbing hook protrudes 0.25 mm to 1.5 mm laterally from the lateral surface of the slender element. In another embodiment, a grabbing hook protrudes 0.5 mm to 1.2 mm laterally from the lateral surface of the slender element.

In another embodiment, the distal end of a grabbing hook protrudes outwardly from the expansion plane of the retractor. In another embodiment, the expansion plane of the retractor is the plane of retraction. In another embodiment, the distal end of a grabbing hook protrudes inwardly from the expansion plane of the retractor. In another embodiment, the distal end of a grabbing hook protrudes perpendicularly from the expansion plane of the retractor. In another embodiment, the distal end of a grabbing hook protrudes up to 90° from the expansion plane of the retractor. In another embodiment, the distal end of a grabbing hook protrudes up to 80° from the expansion plane of the retractor. In another embodiment, the distal end of a grabbing hook protrudes up to 70° from the expansion plane of the retractor. In another embodiment, the distal end of a grabbing hook protrudes up to 60° from the expansion plane of the retractor. In another embodiment, the distal end of a grabbing hook protrudes up to 50° from the expansion plane of the retractor. In another embodiment, the distal end of a grabbing hook protrudes at least 30° from the expansion plane of the retractor. In another embodiment, the distal end of a grabbing hook protrudes at least 40° from the expansion plane of the retractor. In another embodiment, the distal end of a grabbing hook protrudes at least 50° from the expansion plane of the retractor. In another embodiment, the distal end of a grabbing hook protrudes at least 60° from the expansion plane of the retractor. In another embodiment, the distal end of a grabbing hook protrudes at least 70° from the expansion plane of the retractor.

In another embodiment, the maximal distance between the distal ends of the slender elements is 10 mm. In another embodiment, the maximal distance between the distal ends of the slender elements is 9 mm. In another embodiment, the maximal distance between the distal ends of the slender elements is 7 mm. In another embodiment, the maximal distance between the distal ends of the slender elements is 6 mm. In another embodiment, the maximal distance between the distal ends of the slender elements is 5 mm. In another embodiment, the maximal distance between the distal ends of the slender elements is 4 mm. In another embodiment, the maximal distance is obtained in the fully expanded position of the retractor.

In another embodiment, the distal end of a grabbing hook is the distal end of the retractor. In another embodiment, the distal portion of the retractor is a portion of the retractor extending from the joining mechanism, pivot, and/or spring to the distal end of the retractor.

In another embodiment, a grabbing hook defines a niche having a maximal depth 0.1 mm to 1.8 mm. In another embodiment, a grabbing hook defines a niche having a maximal depth 0.1 mm to 1.5 mm. In another embodiment, a grabbing hook defines a niche having a maximal depth 0.3 mm to 1.2 mm. In another embodiment, a grabbing hook defines a niche having a maximal depth 0.5 mm to 1 mm.

Figure 2A:
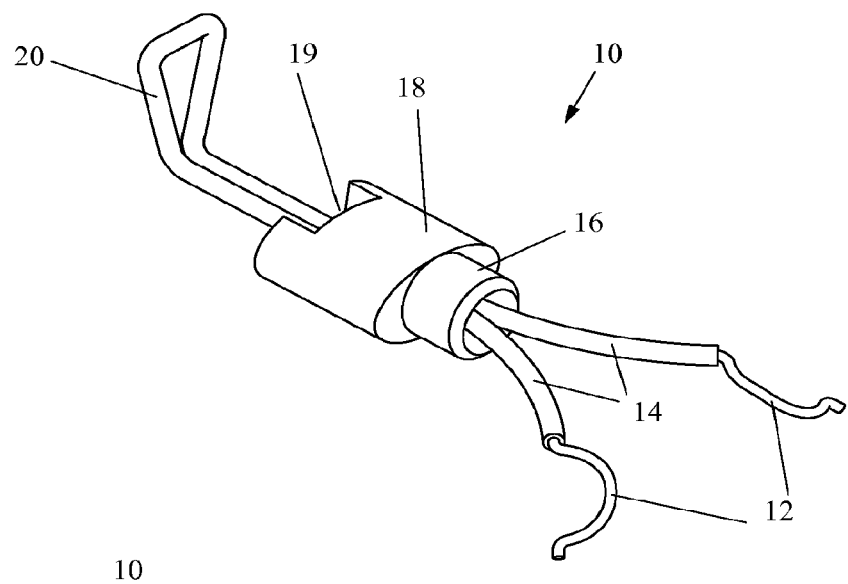
FIGS. 2A-2C are simplified perspective, side-view and top-view illustrations, respectively, of the iris retractor of FIGS. 1A-1C, in a partially expanded orientation, in accordance with an embodiment of the present invention.
Figure 2B:
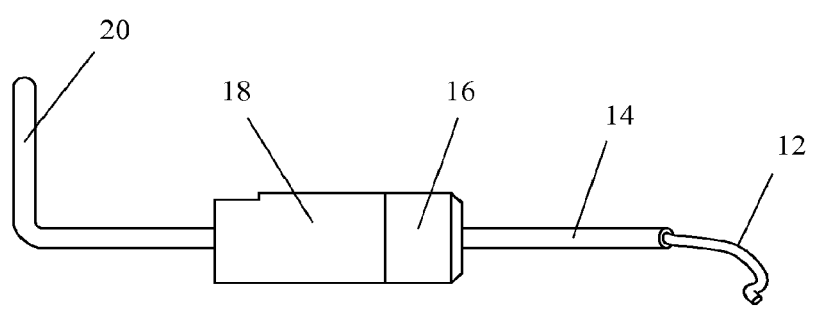
Figure 2C:
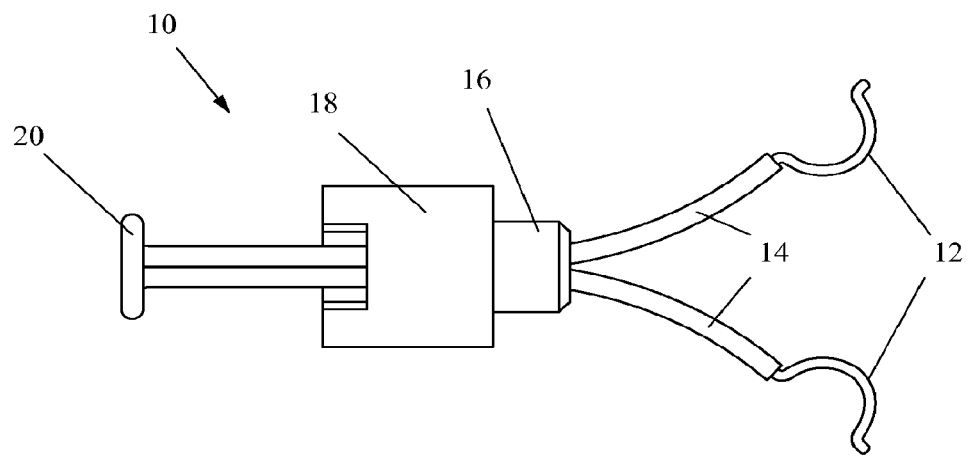
Figure 3A:
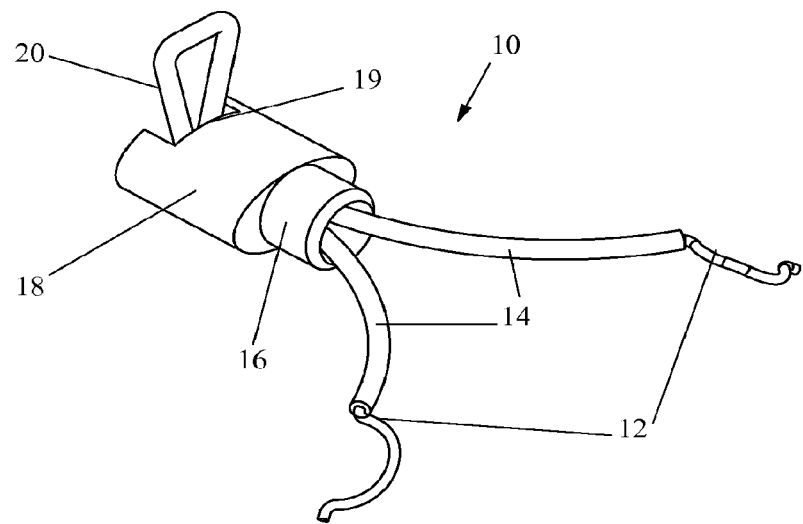
FIGS. 3A-3C are simplified perspective, side-view and top-view illustrations, respectively, of the iris retractor of FIGS. 1A-1C, in a fully expanded orientation, in accordance with an embodiment of the present invention.
Figure 3B:
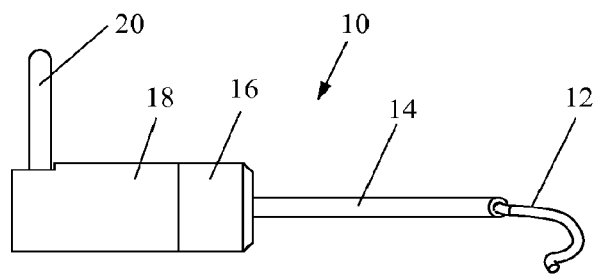
Figure 3C:
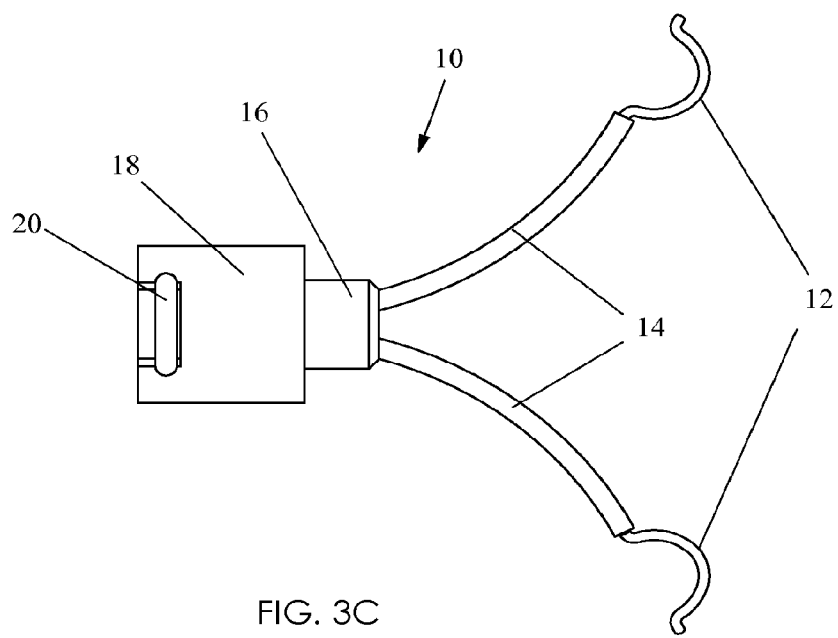

In the illustrated embodiment, there are two slender elements (such as but not limited to 14). The slender elements 14 are arranged to move through a retaining element 16 from a fully retracted position (FIGS. 1A-1C) to a partially expanded position (FIGS. 2A-2C) to a fully expanded position (FIGS. 3A-3C). A proximal portion 18 of retaining element 16 is formed with a groove 19. The proximal ends of slender elements 14 terminate in a proximal handle 20. The slender elements 14 may be joined as a single element before connection to handle 20 or may be joined at the handle 20. In the fully expanded position, handle 20 is pushed completely into groove 19 and is squeezed and held in this position by the side walls of groove 19. (Alternatively, handle 20 may "click" into groove 19. Accordingly, there can be a fixed configuration, wherein handle 20 clicks into groove 19 and slender elements 14 have a fixed expansion, or an adjustable expansion configuration, wherein the more the slender elements 14 are inserted into the eye (such as proximal portion 18) the larger is their lateral expansion. Retaining element 18 retains slender elements 14 in the retracted position until handle 20 is pushed towards groove 19. In one embodiment, the slender elements are retained by element 18 and are formed to expand.

Slender elements 14 and hooks 12 may be constructed of a metal or plastic wire, such as but not limited, NITINOL or stainless steel or a medically safe plastic with suitable resilience, e.g., a shape memory polymer plastic.

In another embodiment, a retractor of the invention comprises two joined slender elements. In another embodiment, joined slender elements are directly or indirectly joined. In another embodiment, joined slender elements are joined by a pivot. In another embodiment, joined slender elements are joined by a spring. In another embodiment, the spring is a spring retaining element. In another embodiment, a spring retaining element retains the retractor in an expanded configuration/position. In another embodiment, upon exertion of force which brings the slender elements into proximity (non-expanded to retracted position) the distance between the attachment points of the spring within the slender elements-shortens. In another embodiment, upon exertion of force which brings the slender elements into proximity (non-expanded to retracted position) the spring bends. In another embodiment, joined slender elements are joined by a pivot and/or a spring. In another embodiment, joined is joined at the proximal portion of the slender elements. In another embodiment, the length of a slender element is divided to 2 equal (in length) parts a "proximal portion" (adjacent to the handle) and a "distal portion" (adjacent to the iris grabbing tooth or hook).

In another embodiment, the retractor described herein substantially reduces the medical complications associated with intraocular surgery. In another embodiment, the retractor described herein substantially reduces the medical complications associated with cataract surgery.

In another embodiment, the retractor described herein is utilized for pupil dilation, based on a concept different than any other device in the market. In another embodiment, the invention is utilized by using a pair of retractors which are inserted through two 19 Gauge or 0.3-5 mm side-port incisions, typically placed one opposite to the other. In another embodiment, the invention is utilized by using a pair of retractors which are inserted through two 19 Gauge or 0.3-3.5 mm side-port incisions, typically placed one opposite to the other.

In another embodiment, each retractor is inserted with its two arms (also referred to a "slender elements") firmly closed, in a fully retracted configuration using designated forceps. In another embodiment, the bulge (also referred to as ear) within each slender element is used for securing and/or anchoring a retractor of the invention to forceps (utilized for insertion of the retractor into the eye. In another embodiment, each of the grabbing hooks anchor a pupillary margin. In another embodiment, once the slender elements (two arms) of the retractor are in position, the forceps are gently released to allow a smooth and control opening of the retractor to a fully expanded configuration. In another embodiment, this release of the retracted configuration to the expanded configuration results in dilating the pupil to create a 2×2 to 12×12 mm quadrangular opening. In another embodiment, this release of the retracted configuration to the expanded configuration results in dilating the pupil to create a 3×3 to 10×10 mm quadrangular opening. In another embodiment, the quadrangular opening is 6×6 mm+/−40%.

In another embodiment, provided herein a method for dilating a pupil in a subject in need thereof, comprising: (a) performing two opposing 0.5 to 4 mm long incisions in the cornea; (b) inserting through each one of the 0.5 to 4 mm long incisions an iris retractor in a fully retracted configuration; (c) positioning the distal end of the iris retractor behind the iris; (d) expanding the iris retractor (by releasing the grip from the forceps and allowing the expansion of the retractor); wherein the iris retractor comprises: two slender elements operatively coupled via a joining mechanism, wherein each slender element comprises: an iris grabbing hook located at the distal portion of said slender element; and a handle located at the proximal portion of the slender element, wherein the joining mechanism is configured to endow the iris retractor with at least two configuration: a retracted configuration and an expanded configuration, wherein the length of each slender element is between 4 mm to 15 mm.

In some embodiments, "positioning the distal end" includes partial expansion of the retractor. In some embodiments, "expanding the iris retractor" is fully expanding the iris retractor. In some embodiments, the actual degree of "fully expanding" is dependent on tissue expansion resistance of the iris or the retractor's mechanical limitation.

In another embodiment, provided herein a method for dilating a pupil in a subject in need thereof, comprising: (a) performing two opposing 0.5 to 4 mm long incisions in the cornea; (b) inserting through each one of the 0.5 to 4 mm long incisions an iris retractor in a fully retracted configuration; (c) positioning the distal end of the iris retractor behind the iris; (d) expanding said iris retractor; wherein the iris retractor comprises: two slender elements operatively connected to one another.

In another embodiment, surgical maneuvers can then be performed using routine techniques under direct visualizations. In another embodiment, at the end of the surgery both retractors are removed using the forceps—the slender elements (two arms) are pushed to a fully retracted configuration and the retractor is simply pulled out via the aforementioned incision.

In another embodiment, the location of the side port incisions determines the shape of the pupillary opening. In another embodiment, asymmetrical, non-opposite, location of the incisions results in a trapezoidal opening with its wider base facing the surgeon (this provides a wide "device free" area in which the slender elements do not impede with the access of surgical instruments.

In another embodiment, side port incisions are done parallel to the iris plan. In another embodiment, the grabbing hooks are bent backward (protrude laterally). In another embodiment, the slender elements are only partially expanded to approximately the diameter of the constricted pupil, the grabbing hooks are positioned properly behind the iris and only then the device is released to its full expansion.

In another embodiment, a device is released to its full expansion and/or extension is a fully expanded device. In another embodiment, expansion of the device is forced by the spring. In another embodiment, the spring's force is smaller than the tissue's tearing force. In another embodiment, the spring's force is smaller than the cornea's tearing force.

In another embodiment, the distance between the distal ends of a fully expanded retractor is 4 to 15 mm. In another embodiment, the distance between the distal ends of a fully expanded retractor is 4 to 12 mm. In another embodiment, the distance between the distal ends of a fully expanded retractor is 5 to 10 mm. In another embodiment, the distance between the distal ends of a fully expanded retractor is 5.5 to 8 mm. In another embodiment, the distance between the distal ends of a fully expanded retractor is 2.5 to 6 mm.

In another embodiment, the spring's force is 0.4 to 25 grams. In another embodiment, the spring's force is 0.5 to 20 grams. In another embodiment, the spring's force is 1 to 15 grams. In another embodiment, the spring's force is 1.5 to 15 grams. In another embodiment, the spring's force is 1 to 15 grams. In another embodiment, the spring's force is 1.5 to 6 grams.

In another embodiment, the spring's force is 1 to 10 grams when the distance between the distal ends of the retractor is 4 to 10 mm. In another embodiment, the spring's force is 1 to 8 grams when the distance between the distal ends of the retractor is 5 to 8 mm. In another embodiment, the spring's force is 3 to 10 grams when the distance between the distal ends of the retractor is 5 to 7 mm. In another embodiment, the spring's force is 4 to 9 grams when the distance between the distal ends of the retractor is 4 to 7 mm. In another embodiment, the spring's force is 5 to 14 grams when the distance between the distal ends of the retractor is 4 to 6 mm. In another embodiment, the spring's force is 5 to 11 grams when the distance between the distal ends of the retractor is 3.5 to 5 mm. In another embodiment, the spring's force is 5 to 14 grams when the distance between the distal ends of the retractor is 3 to 4.5 mm. In another embodiment, the spring's force is 5 to 12 grams when the distance between the distal ends of the retractor is 3 to 4 mm. In another embodiment, the spring's force is 6 to 16 grams when the distance between the distal ends of the retractor is 3 to 3.8 mm. In another embodiment, the spring's force is 7 to 13 grams when the distance between the distal ends of the retractor is 3.3 to 3.8 mm. In another embodiment, the spring's force is 8 to 16 grams when the distance between the distal ends of the retractor is 2.7 to 3.8 mm. In another embodiment, the spring's force is 8 to 14 grams when the distance between the distal ends of the retractor is 2.7 to 3.8 mm.

In another embodiment, in case a slender element is not positioned properly, it is repositioned by maneuvering the external part of the same slender element. In another embodiment, the retractor of the invention spares the need to perform any intraocular manipulation during: insertion, reposition, or removal of the retractor.

In another embodiment, a pair of retractors for dilating a pupil were used in a variety of medical cases including: pseudoexfoliation syndrome, uveitic cataract, post glaucoma filtration surgery, mature and hypermature densed nuclear cataract, patients with clinical IFIS, secondary implantation of PC-IOLs in aphakic eyes, and operations combined with pars plana vitrectomy.

In another embodiment, a surgery performed with a pair of retractors as described herein are performed in superior, lateral and/or oblique approaches according to surgeons' preference. In another embodiment, a retractor as described herein is made of a medical grade material such as metal and/or plastic.

In one embodiment, a spring includes a first end and a second end, wherein a first end of a spring is coupled to the proximal portion of a first slender element and a second end of a spring is coupled to a the proximal portion of a second slender element. In another embodiment, an end of the spring is coupled, connected, and/or fixed to a spring receiving groove located within a proximal portion of a slender element. In another embodiment the spring is an extension of the proximal ends of the slender elements. In another embodiment, the spring receiving groove is located within or in proximity to a handle located in the proximal portion of each slender element. In another embodiment, a spring connects the slender elements. In another embodiment, a spring is a flexible clip.

In one embodiment, a portion of the retaining element is coupled to the slender element within a groove formed in proximity to a handle. In another embodiment, the handle is received in the groove. In another embodiment, a first end of the retaining element is coupled to a first slender element within a groove formed in proximity to a handle and a second end of the retaining element is coupled to a second slender element within a groove formed in proximity to a handle. In another embodiment, the handle is received in the groove.

In one embodiment, a spring retains the retractor in an expanded position. In one embodiment, the expanded position is the default position. In one embodiment, the retractor is adjusted to a non-expanded position be exerting force on the proximal ends of the slender elements which brings the proximal portion of each slender element into proximity, and the distal portion of the slender elements into proximity. In one embodiment, the retractor is adjusted to a non-expanded position be exerting force which brings the proximal portions of the two slender elements closer to one another. In one embodiment, the retractor is adjusted to a retracted position by exerting force which brings a proximal portion of the two slender elements into contact. In another embodiment, the phrase "a non-expanded position" is synonymous with the phrase "a non-retracted position". In one embodiment, "a non-expanded position" and "a non-retracted position" is any position between the retracted position and expanded position. In one embodiment, a retracted position is a position wherein an angle formed between the slender elements is zero or close to zero. In one embodiment, an expanded position is a position wherein an angle formed between the slender elements is the maximal angle reachable by an intact retractor of the invention. In one embodiment, an expanded position is a position wherein an angle formed between the slender elements is 90° or more. In another embodiment, the terms "position" and "configuration" are used interchangeably.

In another embodiment, the spring loaded is a biasing means and/or a retaining means, such as but not limited to a coil spring or a flexible band or rod.

Figure 1D:
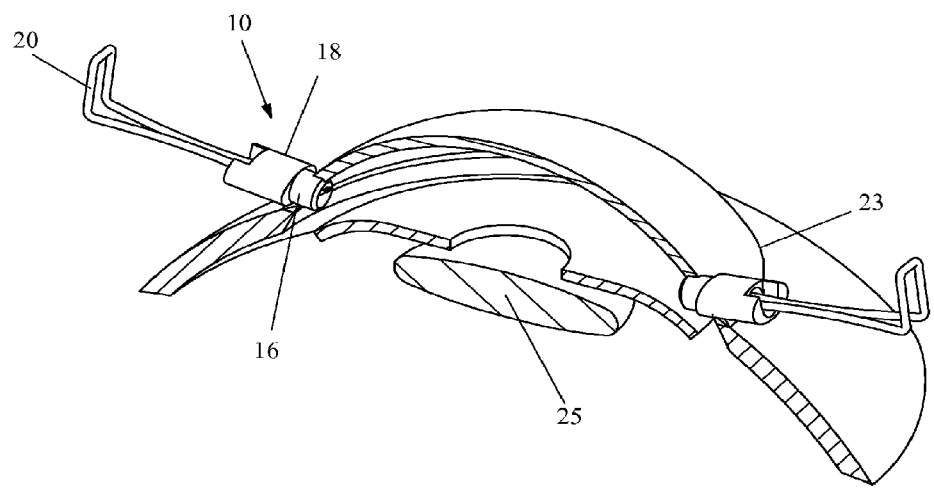
FIGS. 1D-1E are simplified perspective and side-view illustrations, respectively, of the iris retractor of FIGS. 1A-1C used in pairs, in the non-expanded orientation positioned with the distal tip of retaining element (of each retractor) within the incision at the Limbus.
Figure 1E:
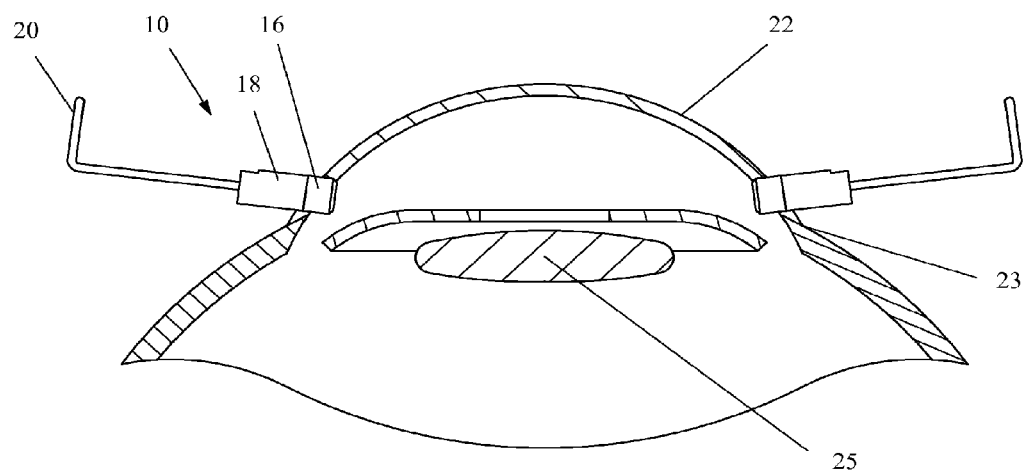

FIGS. 1D-1E illustrate a pair of iris retractors 10 in a non-expanded orientation (i.e., retracted position). A portion of the slender element (such as 18) abuts against the cornea 22, in proximity of up to 8 mm from the limbus 23. As seen in the figures, iris retractor 10 is inserted through a small incision (e.g., 0.5-4.5 mm incision) near the limbus 23.

In some embodiments, the pivot is the narrowest portion of the iris retractor.

Figure 3D:
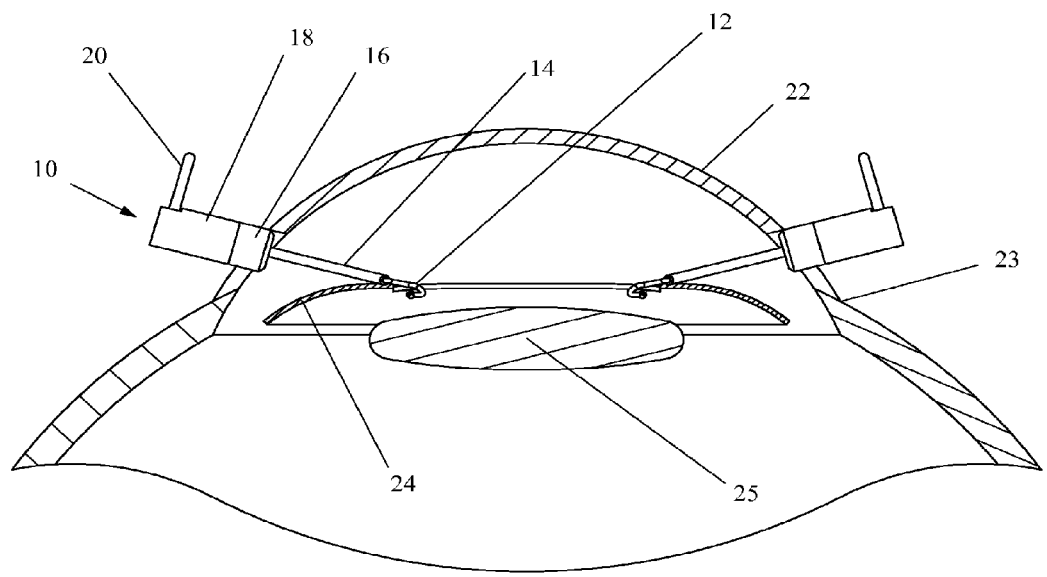
FIGS. 3D-3E are simplified side-view and perspective illustrations, respectively, of the iris retractor of FIGS. 3A-3C used in pairs, each retractor is positioned within the incision with the proximal portion extending outside of the eye and the slender elements within the eye are in the fully expanded orientation (dilated iris)
Figure 3E:
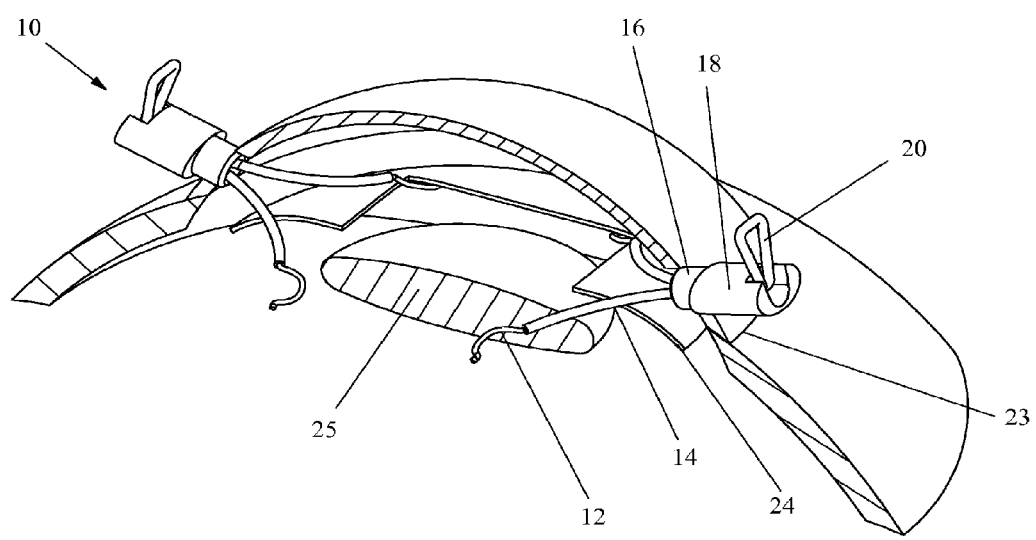

Bringing or squeezing the handles into proximity results in movement the slender elements towards one another—a retracted or a closed position. As seen in FIGS. 3D-3E, hooks (such as 12) grab and hook onto the iris 24 and retract the iris 24 for exposing the lens 25 to provide a good working opening for the surgeon.

The spring anchors and/or holds the retractor in an expanded position by applying a counter force on the outside of the limbus and keeping the retractor in an expanded configuration.

Hooks (such as 12) are separate and spaced apart from each other upon distal movement of slender elements. Thus, a single iris retractor provides spaced apart retraction points, as opposed to some prior art iris retractors which only work at a single point. In another embodiment, the present invention requires 2 iris retractors for providing a proper opening to the surgeon. In another embodiment, the present invention requires 2 iris retractors for providing a proper square shaped opening to the surgeon. In another embodiment, the present invention requires 2 iris retractors for providing a proper rectangle shaped opening to the surgeon.

In another embodiment, the invention provides a kit comprising two or more iris retractor assemblies. In one embodiment, the invention provides a kit comprising: one or more iris retractor assemblies; a holder comprising one or more iris retractor assemblies or holding assemblies (the holding assemblies are configured to hold one or more iris retractor assemblies).

In some embodiment, a pair of iris retractors as described herein is used in kits and in medical procedures as described herein. In another embodiment, an iris retractor is inserted in a non-expanded orientation (i.e., retracted position) and then placed within the eye.

In another embodiment, in a fully retracted position the total width of the slender elements in each iris retractor (FIGS. 1A-1C) is less than 3 mm wide. In another embodiment, the total with of the slender elements in a fully retracted position (FIGS. 1A-1C) is less than 2.5 mm wide. In another embodiment, the total with of the slender elements in a fully retracted position (FIGS. 1A-1C) is less than 2 mm wide. In another embodiment, in a fully retracted position the total width of the slender elements enables the insertion of an iris retractor through a small incision in the limbus. In another embodiment, the small incision is 0.5 to 3.5 mm wide or long, 0.8 to 2.5 mm wide or long, or 0.7 to 1.8 mm wide or long.

In some embodiment, FIGS. 1 and 2 further describe a device of the invention similar to the device of FIG. 1. In some embodiment, a hook as described herein includes a proximal end such as element 703 (FIG. 14A) or element "a" in FIG. 12A, B and FIG. 13A, B. In some embodiment, a hook as described herein includes a midpoint such as element "b" in FIG. 12A, B and FIG. 13A, B. In some embodiment, a hook as described herein includes a distal end such as element 704 (FIG. 14A) or element "c" in FIG. 12A, B and FIG. 13A, B.

Figure 12A:
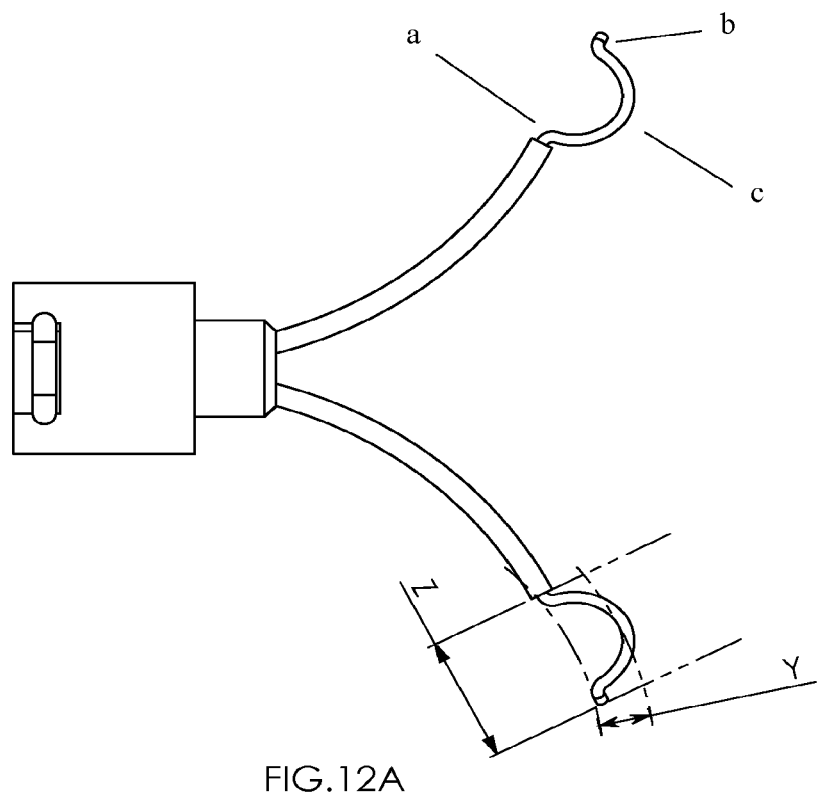
FIGS. 12A-12B are simplified pictorial illustrations of the iris retractor of FIG. 1 providing additional views and measures.
Figure 12B:
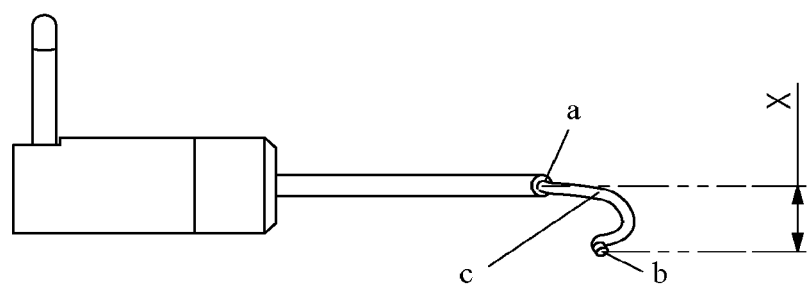
Figure 13A:
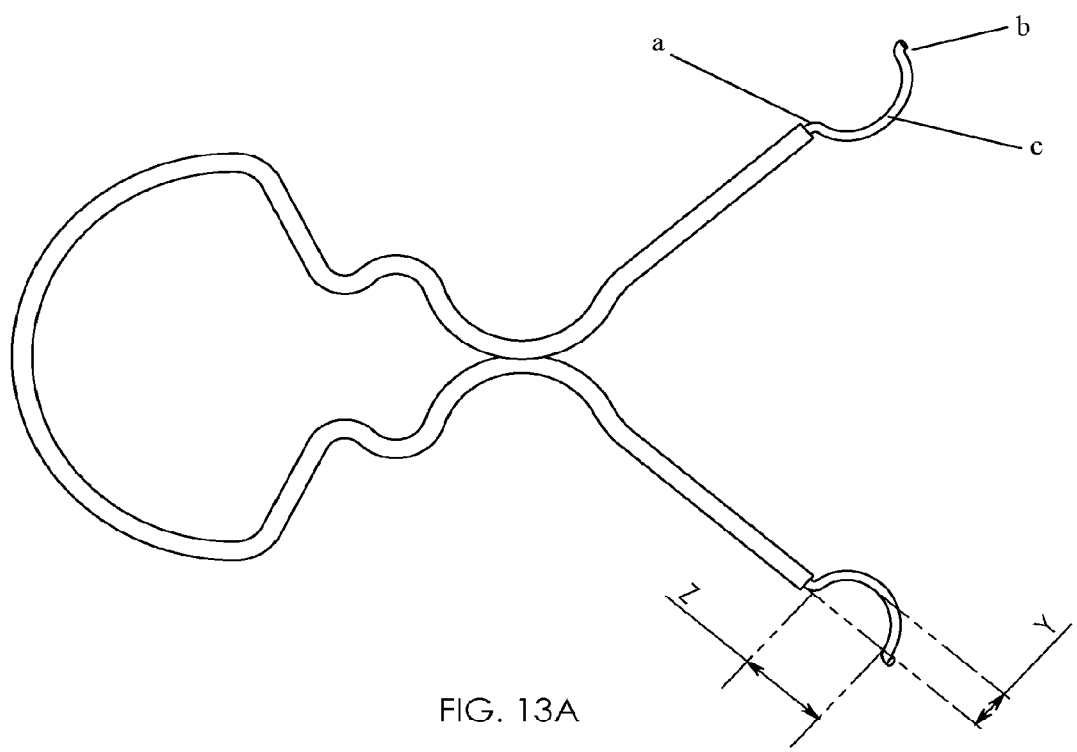
FIGS. 13A-13B are simplified pictorial illustrations of the iris retractor of FIG. 4 providing additional views and measures.

In some embodiment, a hook has an outer length of 0.1 to 2 mm long such as but not limited to "z" in FIG. 12A. In some embodiment, a hook has an outer length of 0.3 to 1 mm long such as but not limited to "z" in FIG. 12A. In some embodiment, a hook is 0.1 to 2 mm deep such as but not limited to "y" in FIG. 12A. In some embodiment, a hook is 0.3 to 1.2 mm deep such as but not limited to "y" in FIG. 12A.

In another embodiment, a pair of iris retractors is utilized in various ophthalmic procedures that require the dilation of the pupil. For example, a lens with a cataract is typically removed from the eye by phacoemulsification. In another embodiment, a pair of iris retractors is inserted (each retractor is inserted separately) into an affected eye thus extending/expanding the pupil during phacoemulsification thereby providing the surgeon with a wide view of the lens. In another embodiment, expanding and/or extending the pupil is retracting the iris with what is referred to as an iris retractor, and holding the iris at its outer edges. In another embodiment, the slender elements are adapted to expand and/or extend the pupil. In another embodiment, the distal ends of the two slender elements are adapted to expand and/or extend the pupil and/or hold the iris at its outer edges. In another embodiment, the proximal handles are not inserted through the limbus incision. In another embodiment, the total width of the proximal handles is more than 2 mm wide. In another embodiment, the total width of the proximal handles is more than 2.5 mm wide. In another embodiment, the total width of the proximal handles is more than 3 mm wide. In another embodiment, the total width of the proximal handles is more than 3.5 mm wide. In another embodiment, the total width of the proximal handles is more than 4 mm wide. In another embodiment, the total width of the proximal handles is 2 to 5 mm wide.

Reference is now made to FIGS. 4A-5E, which illustrate an iris retractor 30, constructed and operative in accordance with another embodiment of the present invention.

Iris retractor 30 includes a plurality of hooks 32 disposed or formed at a distal end of one or more slender elements 34. In the illustrated embodiment, there are two slender elements 34. The proximal ends of slender elements 34 terminate in a proximal handle 40. Handle 40 and slender elements 34 are made of a resilient, flexible material (e.g., metal or plastic) to form a kind of resilient tweezers or pliers.

Figure 4A:
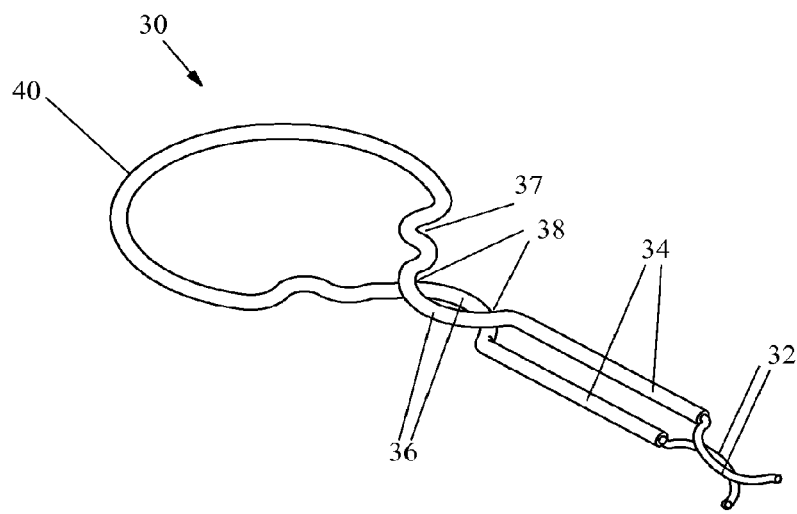
FIGS. 4A-4C are simplified perspective, side-view and top-view illustrations, respectively, of an iris retractor, in a non-expanded orientation, (such as but not limited to as when held by a designated tool for holding and placing an iris), constructed and operative in accordance with another embodiment of the present invention.
Figure 4B:
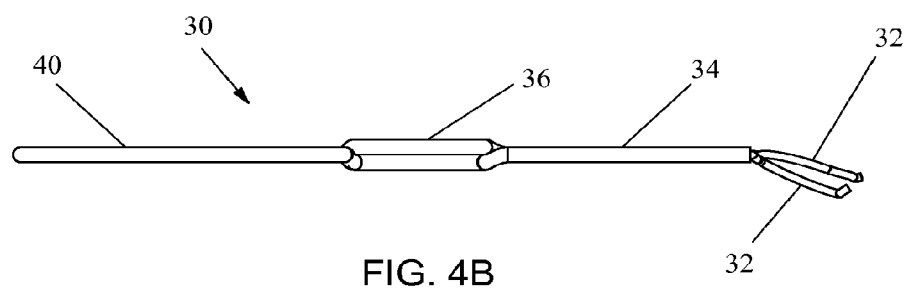
Figure 4C:
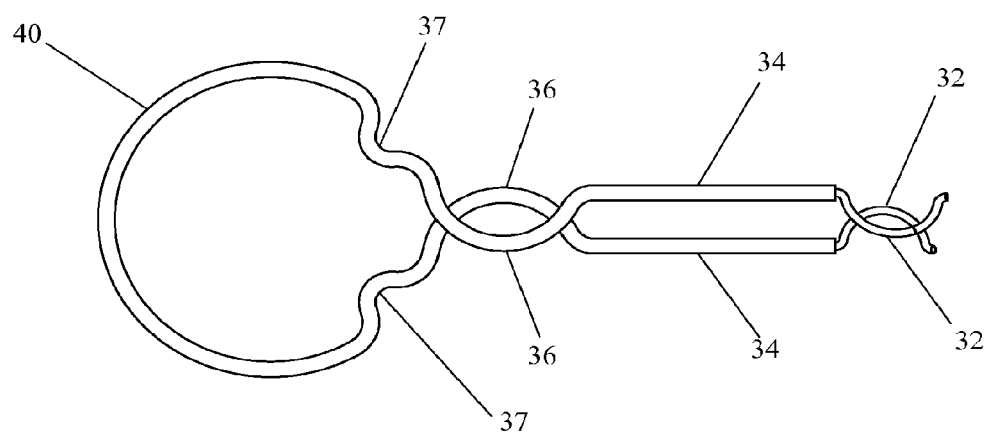
Figure 4D:
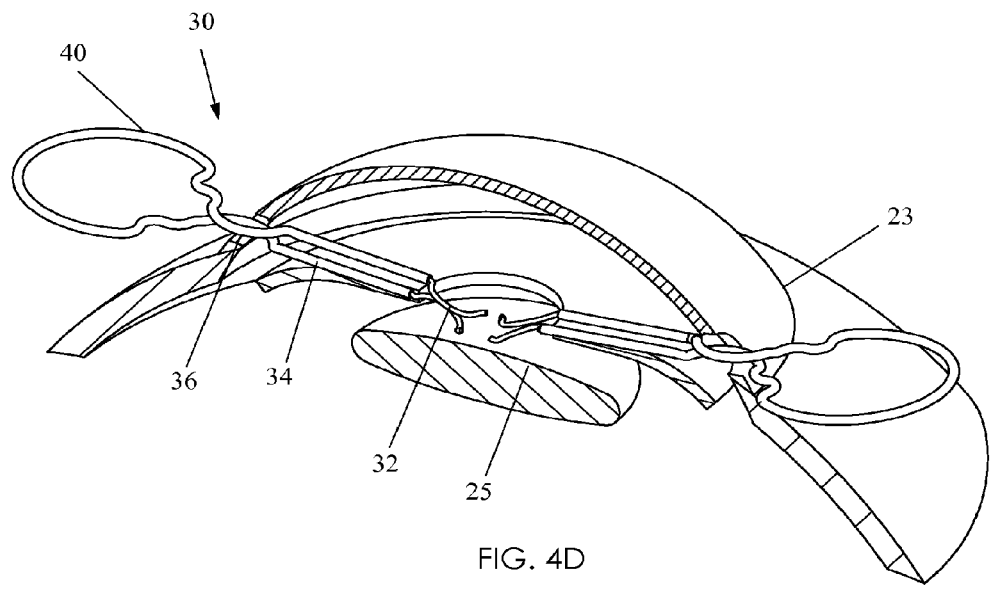
FIGS. 4D-4E are simplified perspective and side-view illustrations, respectively, of the iris retractor of FIGS. 4A-4C used in pairs, each retractor is positioned within and through the incision with the proximal portion outside of the eye and the slender elements within the eye in the non-expanded orientation (such as but not limited to as when held by a designated tool or forceps)
Figure 4E:
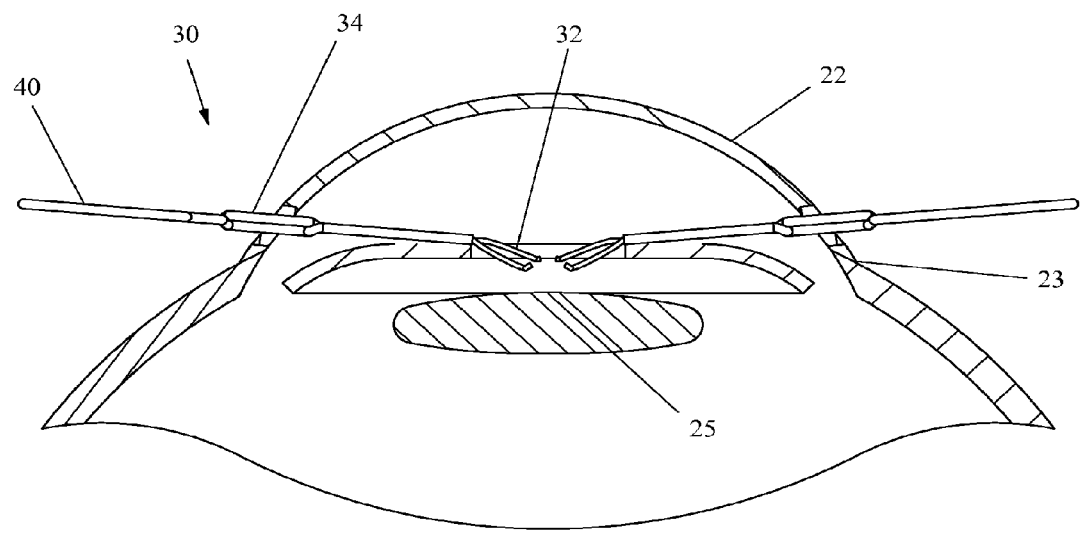

FIGS. 4D-4E illustrate a pair of iris retractors 30 in a non-expanded orientation (i.e., retracted position) placed on the eye. A portion of retaining element 36 (36 is the narrow neck positioned within the incision, its proximal part widens when expanded and abuts against the limbus) abuts against the cornea 22, typically but not necessarily at the limbus 23.

Handle (such as element 40) releases the slender element 34 that is initially caught in groove 38 of retaining element 36. (For the other option mentioned above, iris retractor 30 moves to the expanded position by releasing elements 37.) By virtue of their resilience, slender elements 34 spring outwards to the expanded position in FIGS. 5A-5E. As seen in FIGS. 4A-5E, the geometry of iris retractor 30 enables expansion of hooks 32. In some embodiments, handle 40 is the spring that expands slender element 34. In some embodiments, groove 38 is the narrow neck that remains narrow following expansion in order not to lengthen the incision. In some embodiments, the devices is retracted using a tool and does not have a retracted holding function.

Figure 5A:
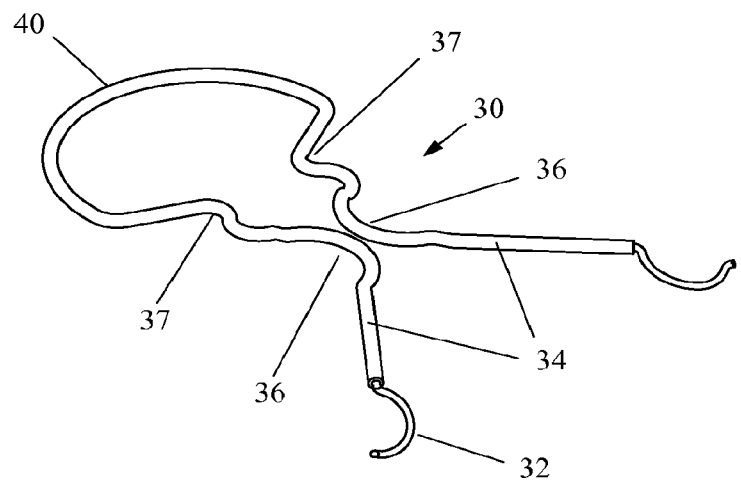
FIGS. 5A-5C are simplified perspective, top-view and side-view illustrations, respectively, of the iris retractor of FIGS. 4A-4C, in an expanded orientation, the non restricted state, in accordance with an embodiment of the present invention.
Figure 5B:
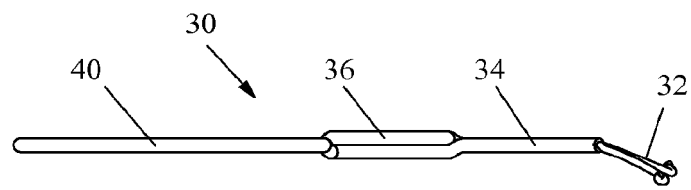
Figure 5C:
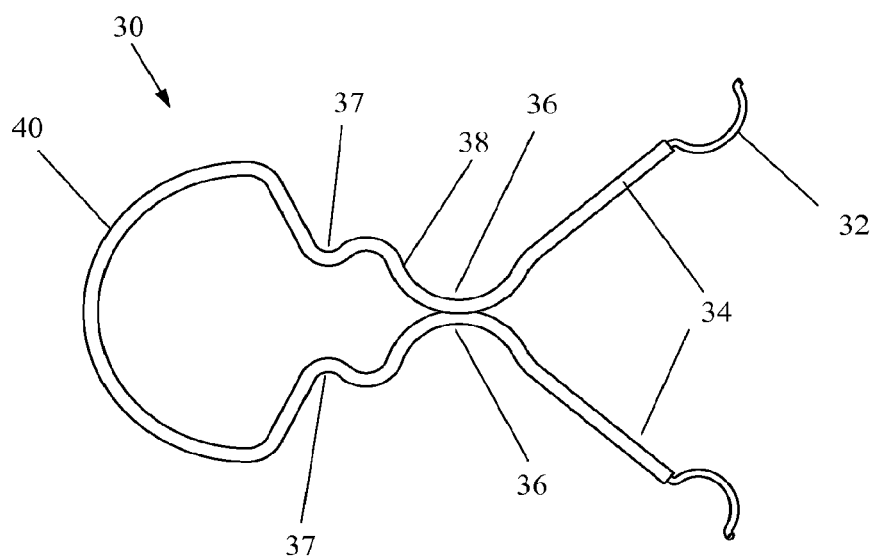
Figure 5D:
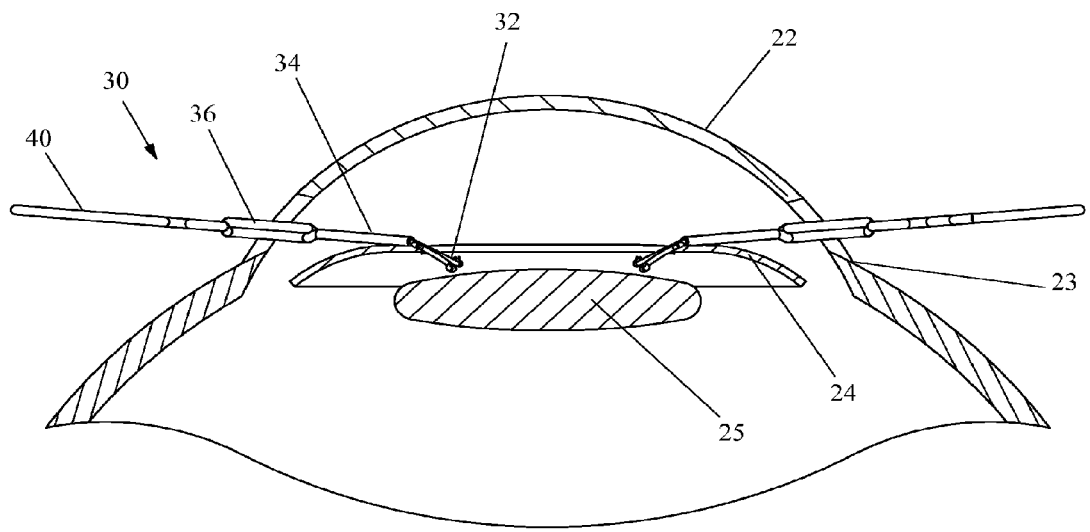
FIGS. 5D-5E are simplified side-view and perspective illustrations, respectively, of the iris retractor of FIGS. 5A-5C used in pairs, each retractor is positioned within the incision with the proximal portion extending outside of the eye and the slender elements within the eye (dilating the iris) in the expanded orientation.
Figure 5E:
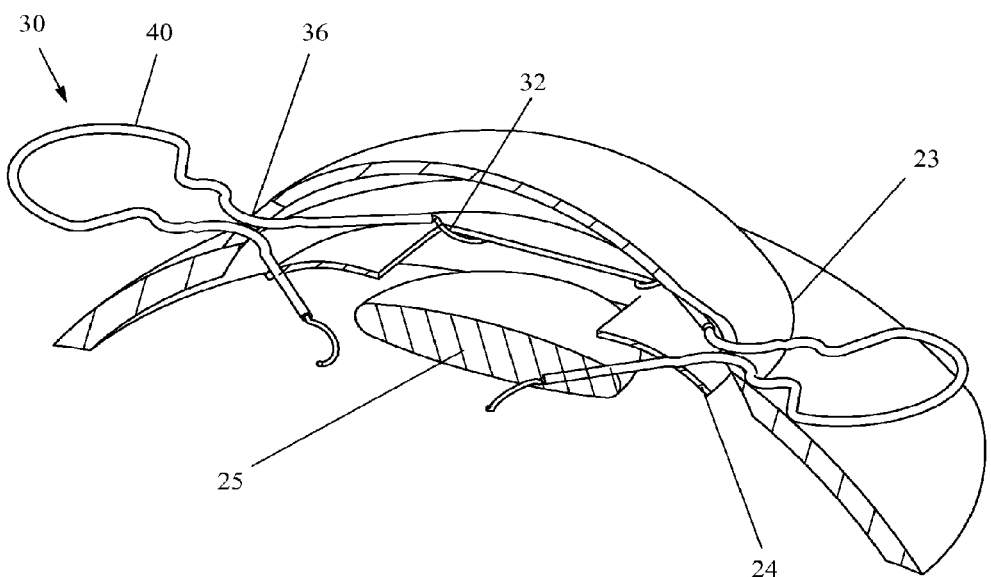

As seen in FIGS. 5D-5E, hooks 32 grab and hook onto the iris 24 and retract the iris 24 for exposing the lens 25 to provide a good working opening for the surgeon.

Reference is now made to FIGS. 6A-7E, which illustrate a pair of iris retractors 50, each retractor is constructed and operative in accordance with yet another embodiment of the present invention.

Iris retractor 50 includes a plurality of hooks 52 disposed or formed at a distal end of one or more slender elements 54. In the illustrated embodiment, there are two slender elements 54, which pivot about a pivot 56. The proximal ends of slender elements 54 terminate in a proximal handle 60. Handle 60, pivot 56 and slender elements 54 form a kind of scissors.

Figure 6A:
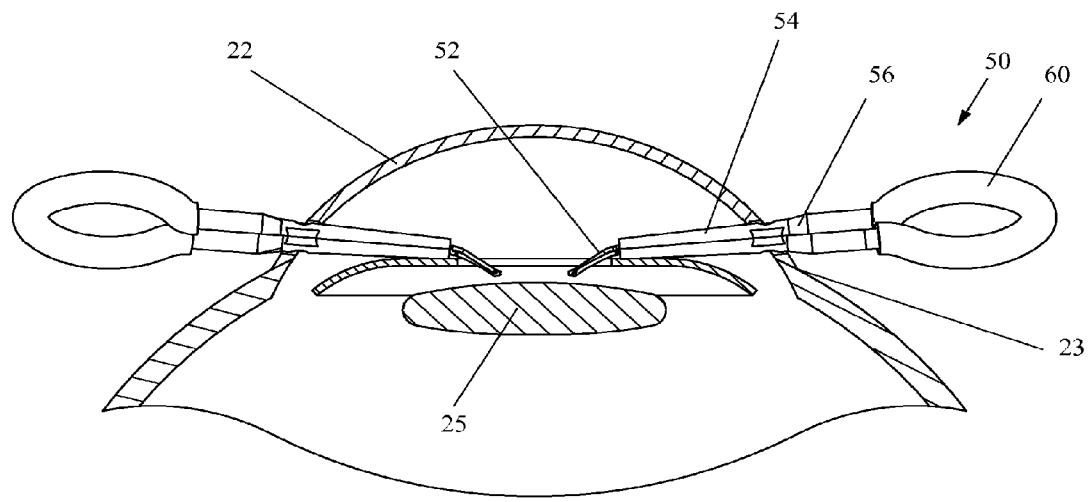
FIGS. 6A-6B are simplified perspective, side-view and top-view illustrations, respectively, of a pair of iris retractors, in a non-expanded orientation, (such as but not limited to as when held by a designated tool or forceps), each retractor is constructed and operative in accordance with yet another embodiment of the present invention.
Figure 6B:
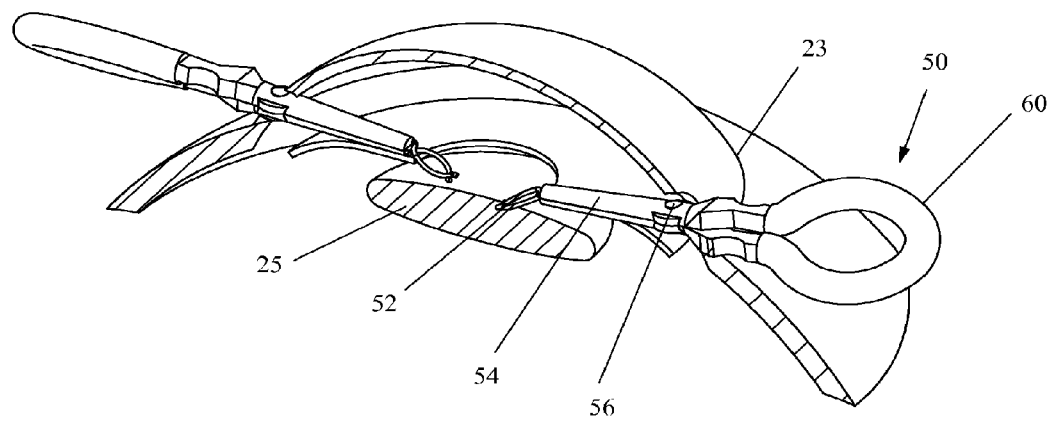

FIGS. 6A-6B illustrate a pair of iris retractors 50 in a non-expanded orientation (i.e., retracted position) placed within the incision, with their slender element within the tissue while the proximal handles remain and/or protrude outside. A portion of iris retractor 50 (e.g., near the pivot 56) abuts against the cornea 22, typically but not necessarily at the limbus 23.

Figure 7A:
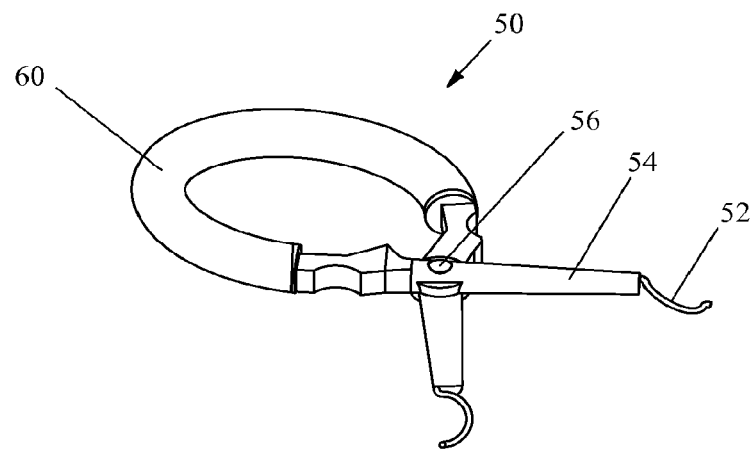
FIGS. 7A-7C are simplified perspective, top-view and side-view illustrations, respectively, of the iris retractor of FIGS. 6A-6C, in an expanded orientation, in accordance with an embodiment of the present invention.
Figure 7B:
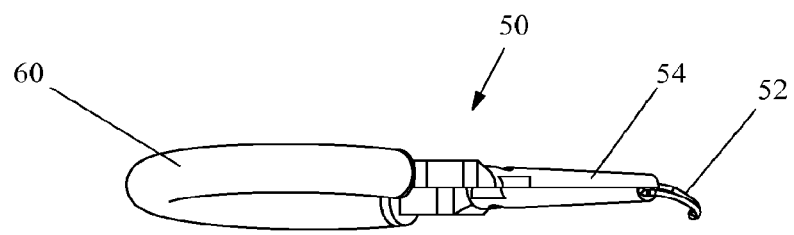
Figure 7C:
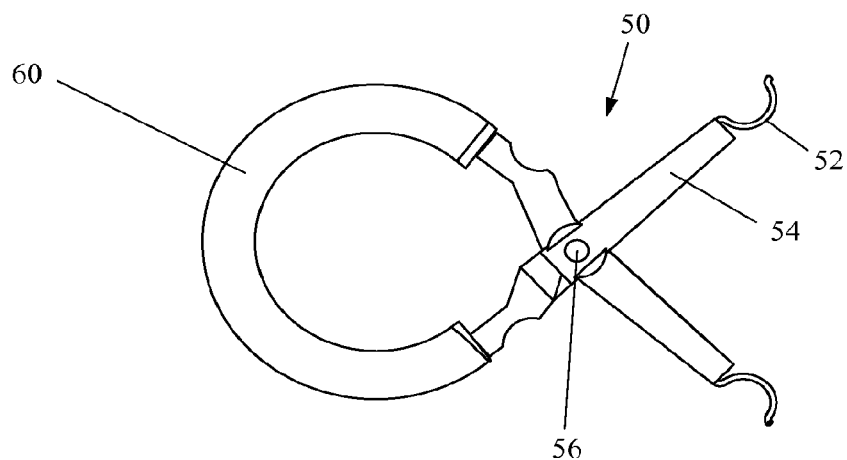
Figure 7D:
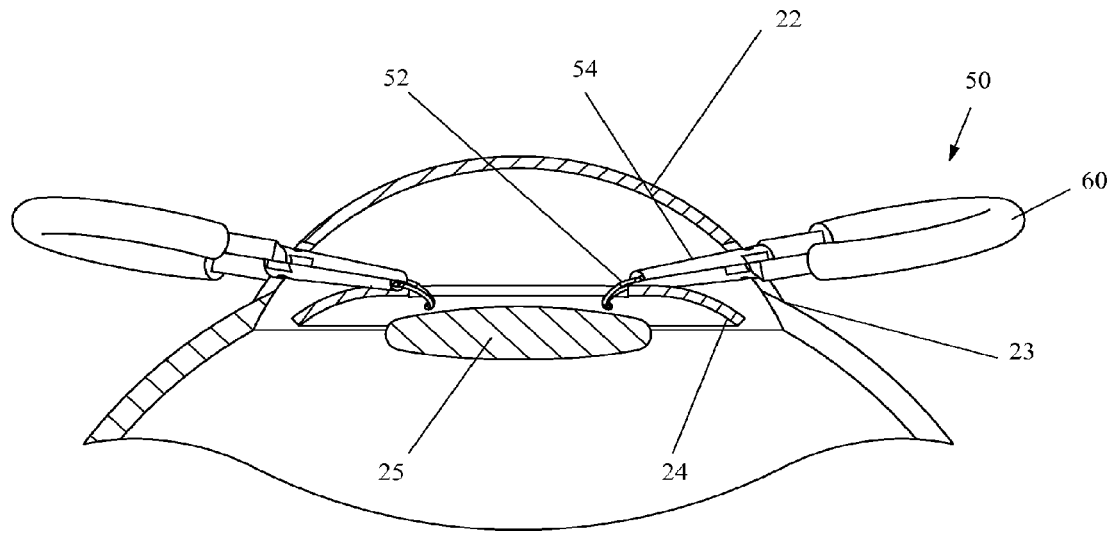
FIGS. 7D-7E are simplified side-view and perspective illustrations, respectively, of a pair of iris retractors of FIGS. 7A-7C, each retractor is positioned within (passed through) the incision with the proximal portion outside of the eye and the slender elements within the eye in the expanded orientation (dilated iris)
Figure 7E:
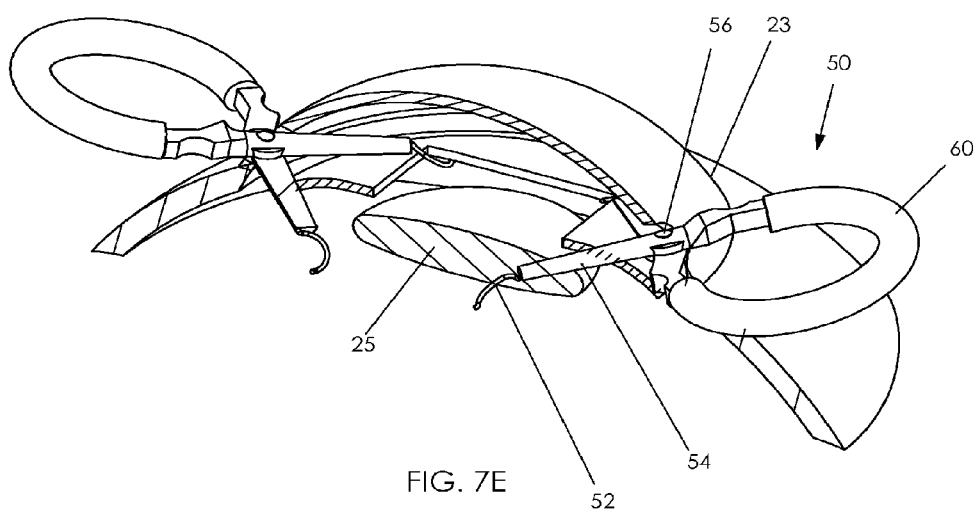

Manipulating handle 60 "scissors out" the slender elements 54 to the expanded position in FIGS. 7A-7E. As seen in FIGS. 7D-7E, hooks 52 grab and hook onto the iris 24 and retract the iris 24 for exposing the lens 25 to provide a good working opening for the surgeon. A portion of iris retractor 50 (e.g., near the pivot 56) anchors the retractor 50 by applying a counter force on the outside of the limbus 23.

Figure 8:
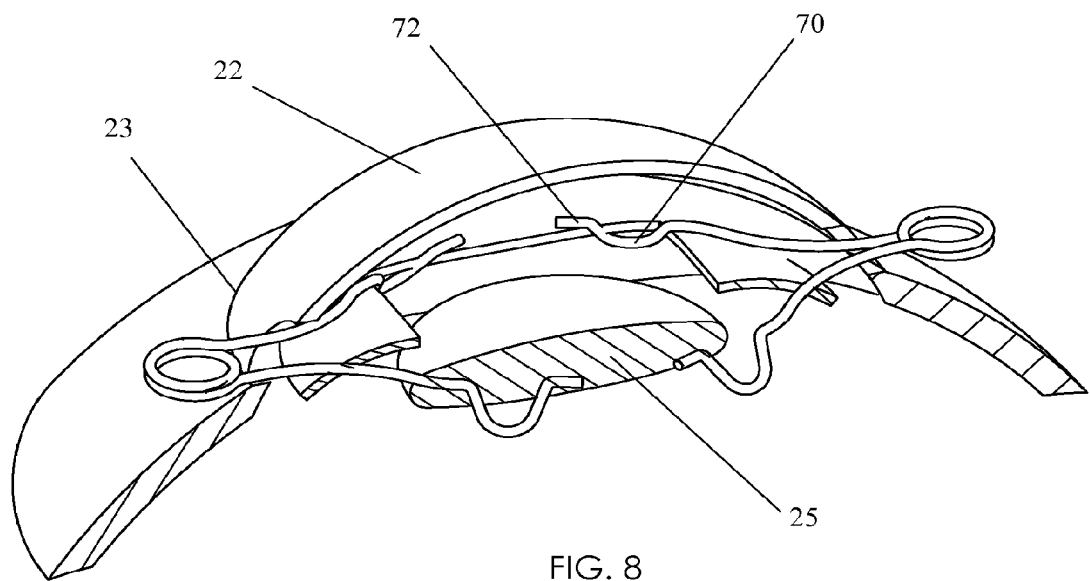
FIG. 8 is a simplified perspective illustrations of a pair of retractors each having a U-shaped tip 70 as a hook with a short distal extension 72.
Figure 9A:
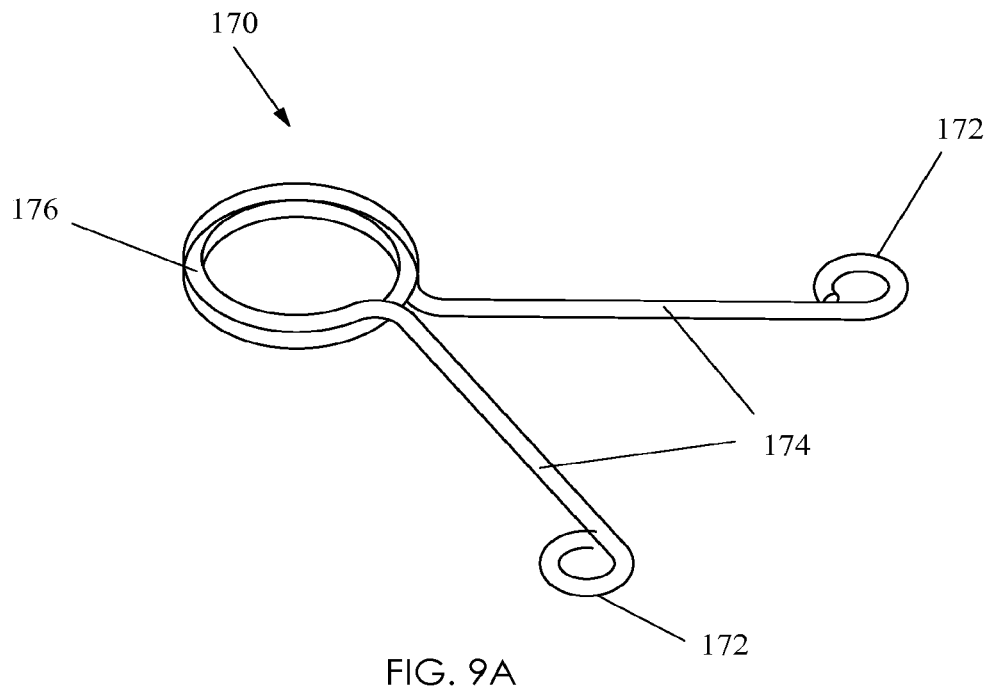
FIG. 9A-9F are simplified perspective illustration of the iris retractor retractor 170, constructed and operative in accordance with another embodiment of the present invention. As seen first slender element are inserted through a small incision at the limbus and are manipulated by the surgeon so that the rounded hooks 172 spread apart and retract the iris.
Figure 9B:
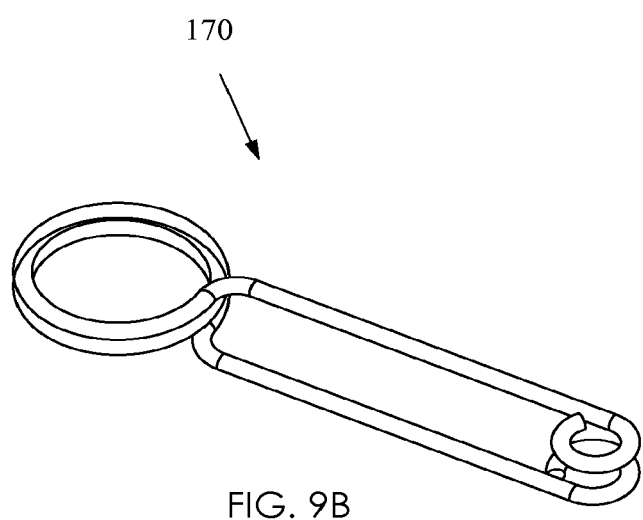
Figure 9C:
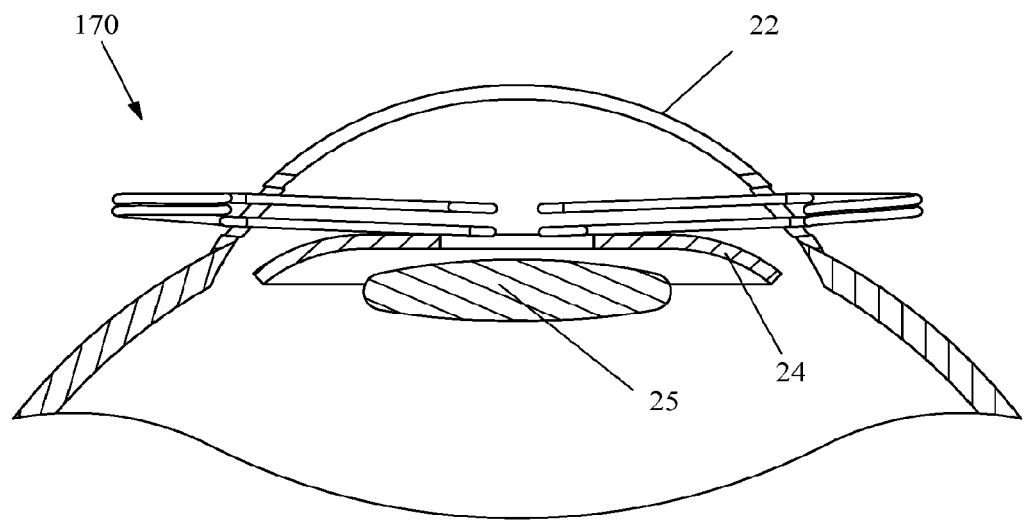
Figure 9D:
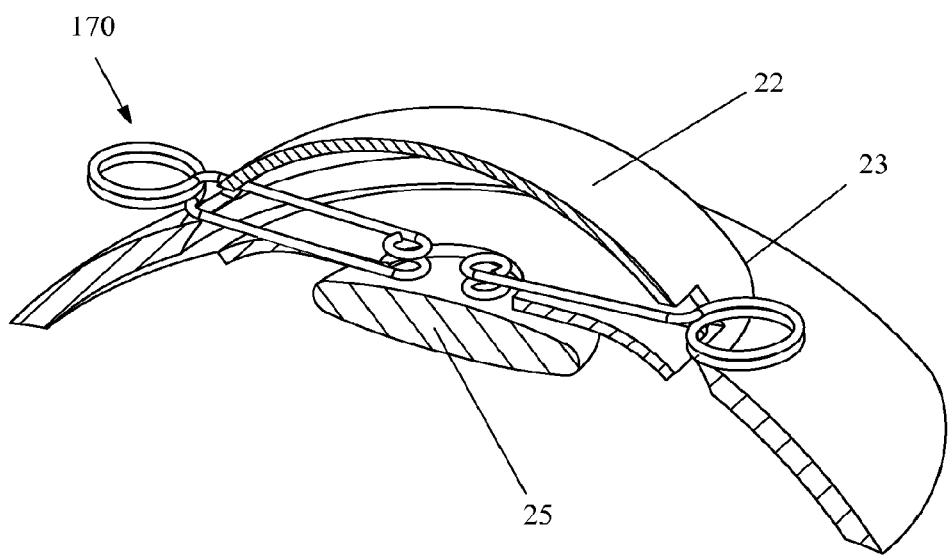
Figure 9E:
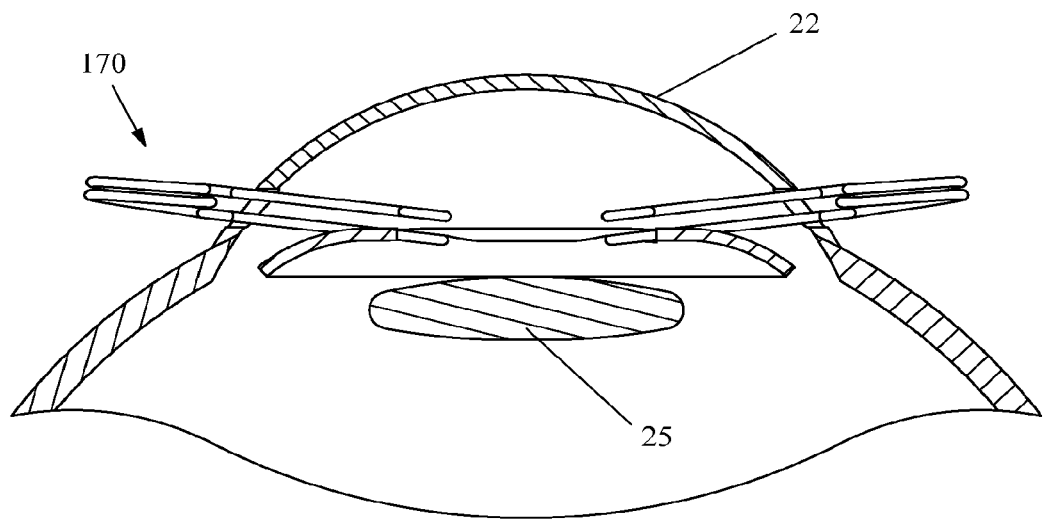
Figure 9F:
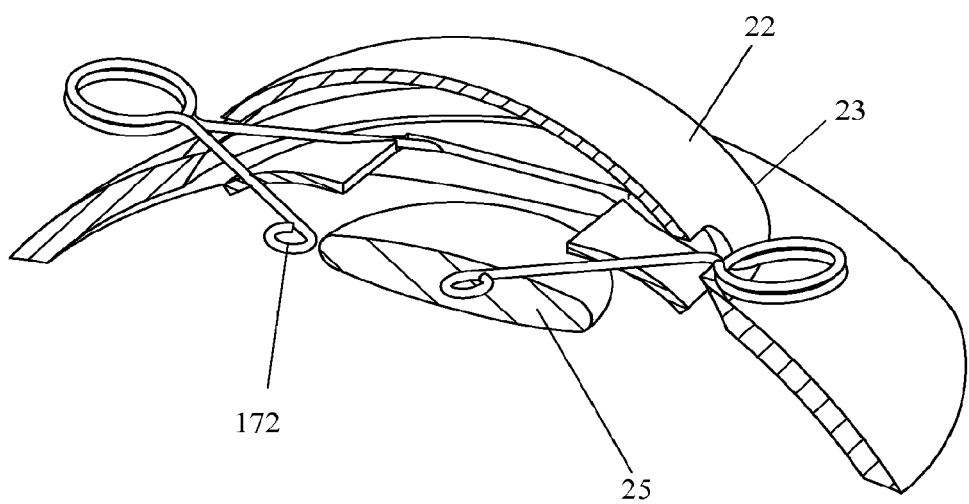

Reference is now made to FIG. 8 which illustrate different tips for the iris retractor of any of the above embodiments, in accordance with different embodiments of the present invention. In FIG. 8, a tip 70 is shown that has a U-shaped hook with a short distal extension 72.

Iris retractor may include a plurality of hooks disposed or formed at distal ends of the slender elements. A slender element, according to some embodiments, may be adjustable in length.

Reference is now made to FIGS. 9A-9F, which illustrate an iris retractor 170, constructed and operative in accordance with another embodiment of the present invention. As seen first slender element are inserted through a small incision at the limbus and are manipulated by the surgeon so that the rounded hooks spread apart and retract the iris.

Iris retractor 170 includes a plurality of hooks 172 disposed or formed at a distal end of one or more slender elements 174. In the illustrated embodiment, there are two slender elements 174. The proximal ends of slender elements 174 terminate in a proximal spring (such as 176). Handle/spring 176 and slender elements 174 are made of a resilient, flexible material (e.g., metal or plastic) to form a kind of resilient tweezers or pliers. The hooks 172 in this embodiment curve back onto slender elements 174 and may optionally abut against slender elements 174. In a non-expanded orientation a pair of iris retractors are inserted through a small incision at the limbus. In some embodiments, iris retractor 170 in an expanded orientation, the hooks 172 grab and hook onto the iris and retract the iris for exposing the lens to provide a good working opening for the surgeon.

Reference is now made to FIGS. 10A-14F, which illustrate an iris retractor 190, constructed and operative in accordance with another embodiment of the present invention.

Figure 10A:
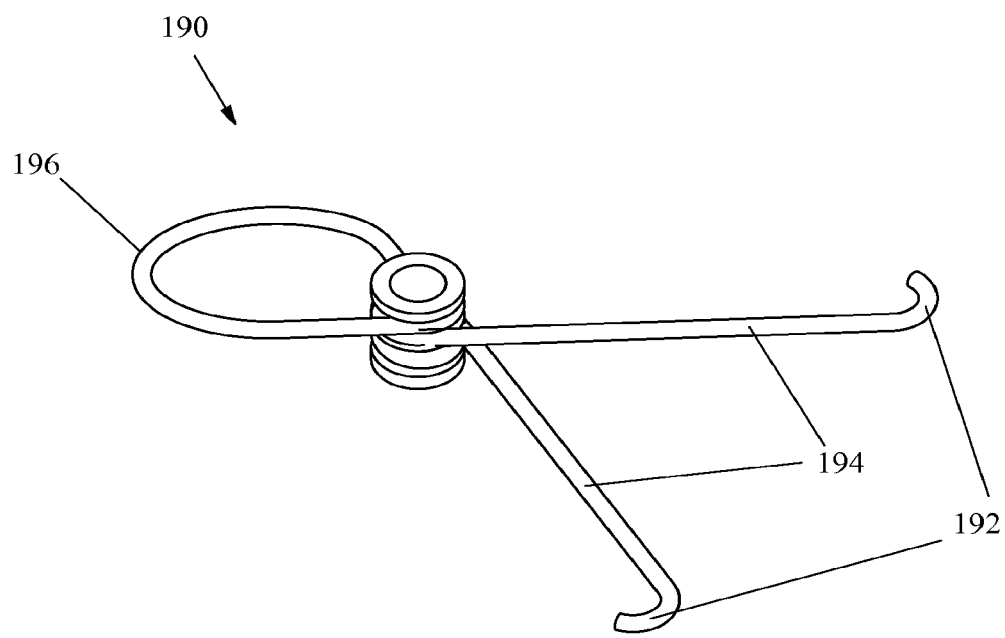
FIGS. 10A-10F are simplified pictorial illustrations of an iris retractor, constructed and operative in accordance with still another embodiment of the present invention.
Figure 10B:
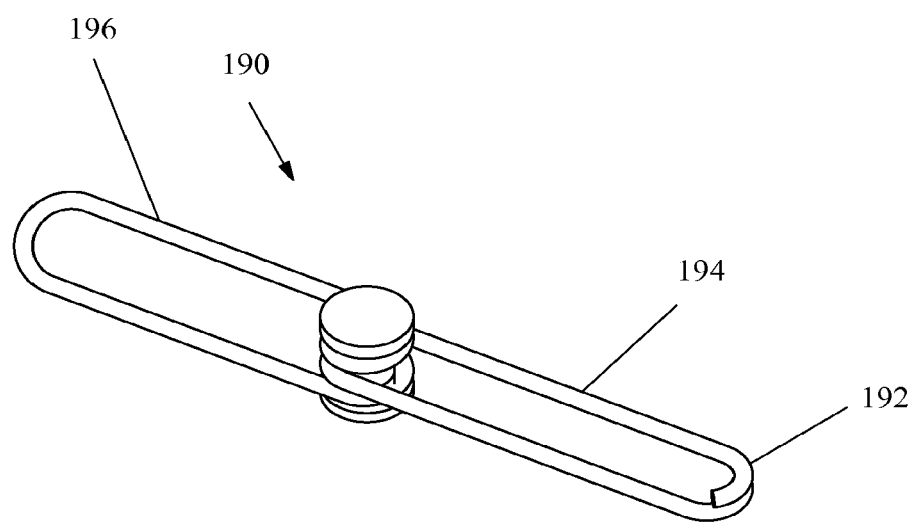
Figure 10C:
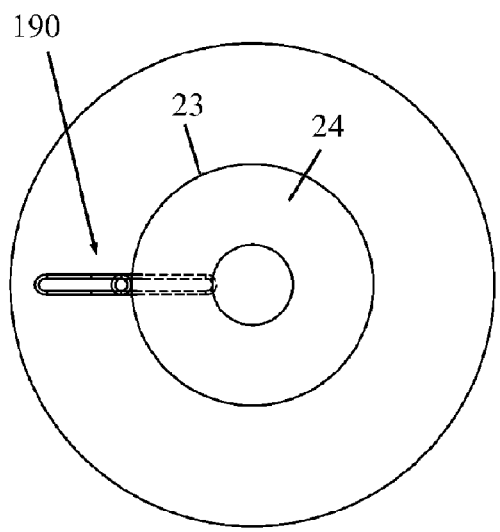
Figure 10D:
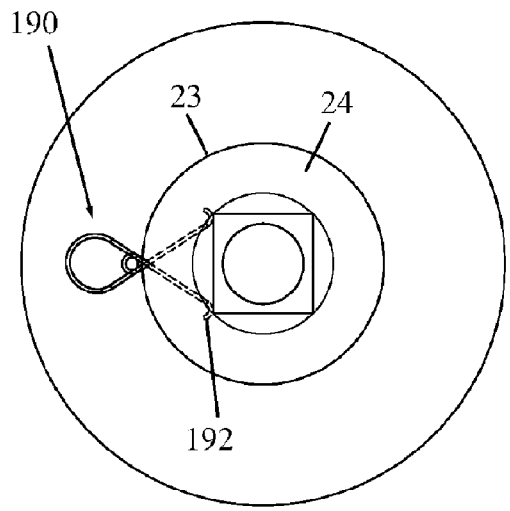
Figure 10E:
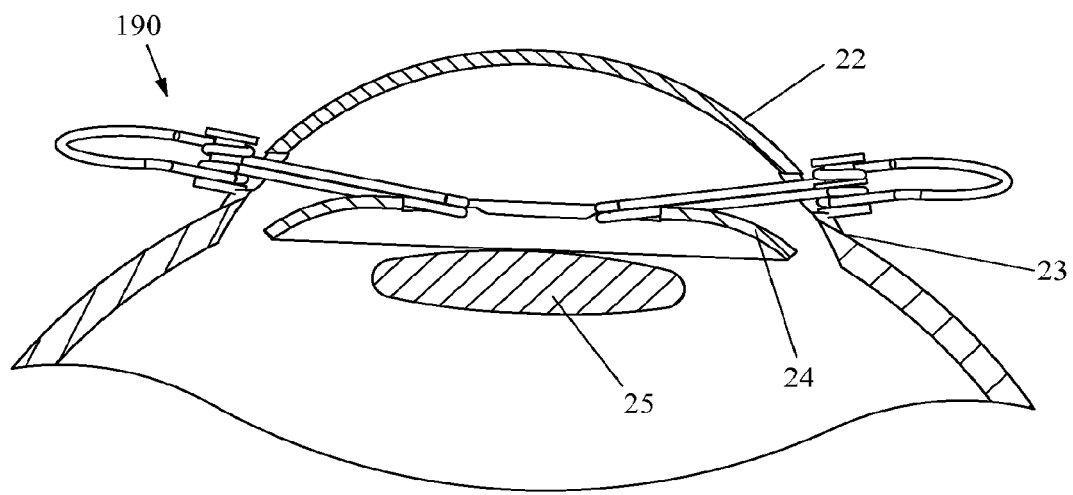

Iris retractor 190 includes a plurality of hooks 192 disposed or formed at a distal end of one or more slender elements 194. In the illustrated embodiment, there are two slender elements 194. The proximal ends of slender elements 194 terminate in a proximal handle 196. Handle 196 and slender elements 194 are made of a resilient, flexible material (e.g., metal or plastic or shape memory) to form a kind of resilient tweezers or pliers. Handle 196 in this embodiment is sufficiently resilient such that it flattens into an oblong shape when squeezed, as seen in FIG. 10B. Handle 196 springs back to its original shape to move iris retractor 190 to the expanded orientation.

Figure 10F:
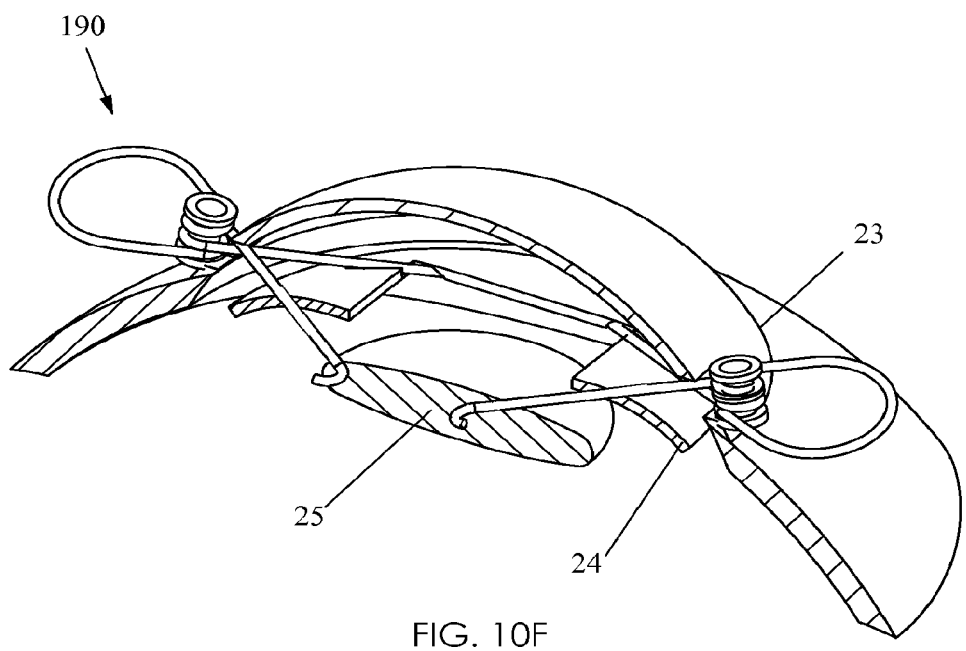

An iris retractor in a non-expanded orientation is inserted through a small incision at the limbus in some embodiments. As mentioned before, handle 196 flattens into an oblong shape. FIG. 10F illustrates iris retractor 190 in an expanded orientation, wherein hooks (element 192 in 10A) grab and hook onto the iris 24 and retract the iris 24 for exposing the lens to provide a good working opening for the surgeon.

Reference is now made to FIGS. 14A-14D, which illustrate an iris retractor 700, constructed and operative in accordance with another embodiment of the present invention. In some embodiments, the iris retractor is composed of two slender elements (702) joined by a pivot (705) and a spring at the proximal end (proximal spring 701). In some embodiments, each slender element ends with a hook formed by two teeth or extensions (703 and 704). In another embodiment, a tissue to be retracted according to the invention is placed in-between extensions (703 and 704) in groove 707. In another embodiment, a tissue to be retracted according to the invention is anchored in-between extensions (703 and 704). In another embodiment, a tissue to be retracted according to the invention is placed over tooth 703 and under tooth 704. In another embodiment, a tissue to be retracted according to the invention is placed over tooth 704 and under tooth 703.

In one embodiment, provided herein an iris retractor comprising: a one piece elastic rod, formed/shaped as a double side by side "L" coupled forms, comprising two slender elements operatively coupled via the proximal section, wherein each slender element (arm) comprises: (1) an iris grabbing hook located at the distal portion or distal end of the slender elements; and (2) a handle located at the proximal portion or proximal end of each of the slender element; and optionally (3) a retaining element, wherein the retaining element is configured to endow the iris retractor with at least two configuration: a retracted configuration and an expanded configuration In some embodiments, a hook is a rounded hook or a crescent-like hook (such as but not limited to element 12 in FIG. 2, FIG. 3, element 192 in FIG. 10. In some embodiments, a hook is bended towards the eye or inwardly such as described herein (see FIG. 3A and/or element 32 in FIG. 5B). In some embodiments, a hook is fully rounded such as in element 172 in FIG. 9.

Reference is now made to FIGS. 11A-11D, which illustrate an iris retractor 200, constructed and operative in accordance with another embodiment of the present invention.

Iris retractor 200 includes a plurality of hooks disposed or formed at a distal end of one or more slender elements. In the illustrated embodiment, there are two slender elements joined by a spring distal to the pivot. The proximal ends of slender elements form a proximal handle that includes two scissor handles. The spring may be loaded by a biasing device, such as a coil spring which has ends attached to each one of the slender elements.

Figure 11A:
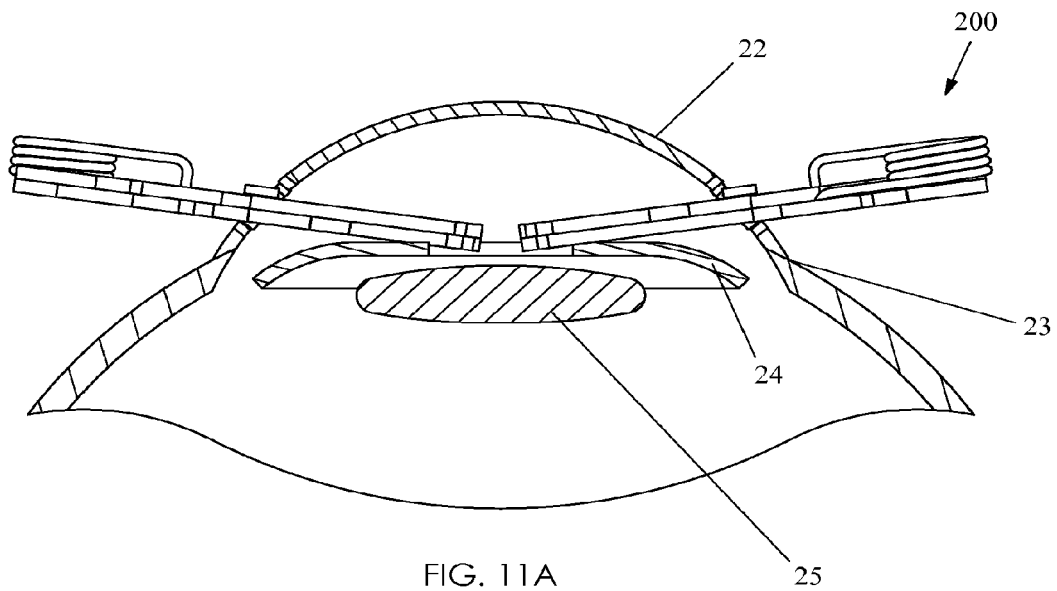
FIGS. 11A-11D are simplified pictorial illustrations of an iris retractor, constructed and operative in accordance with another embodiment of the present invention.
Figure 11B:
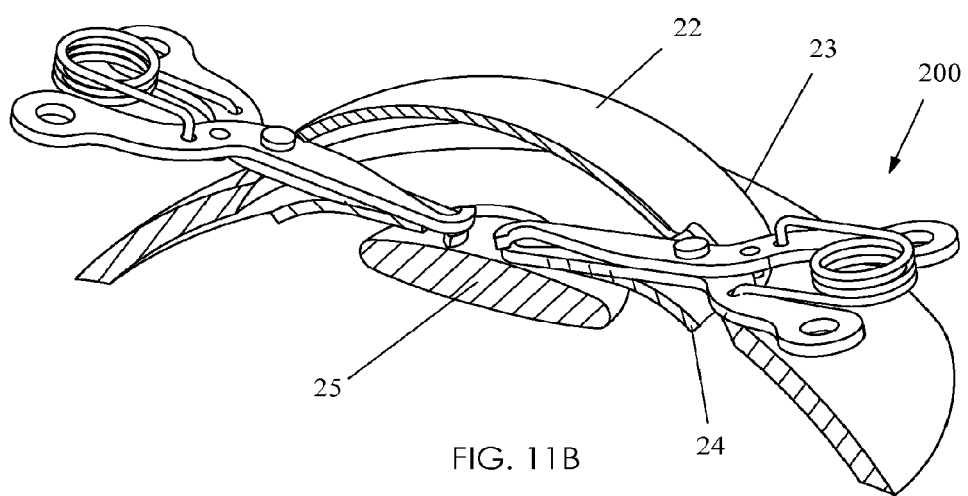
Figure 11C:
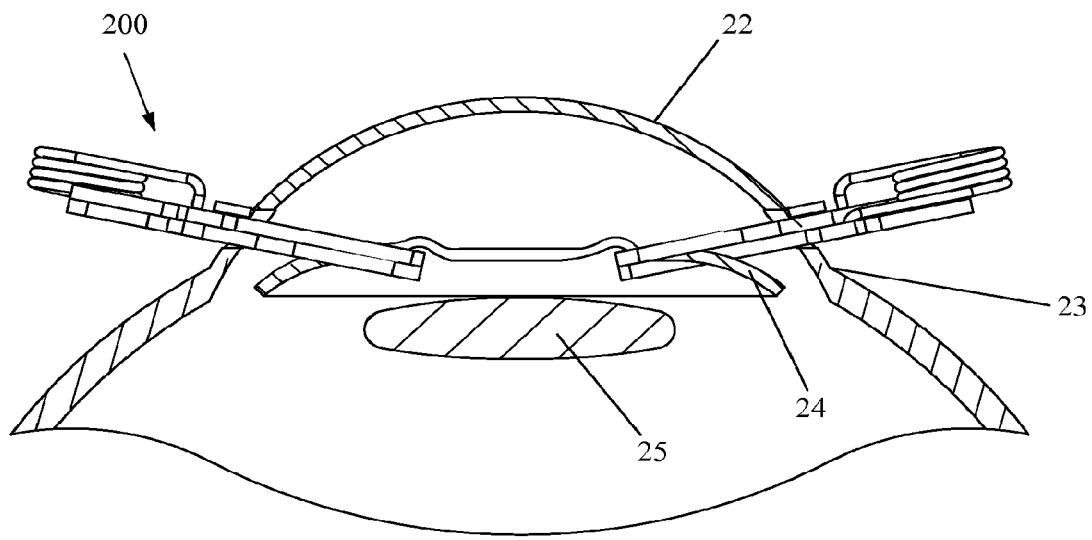
Figure 11D:
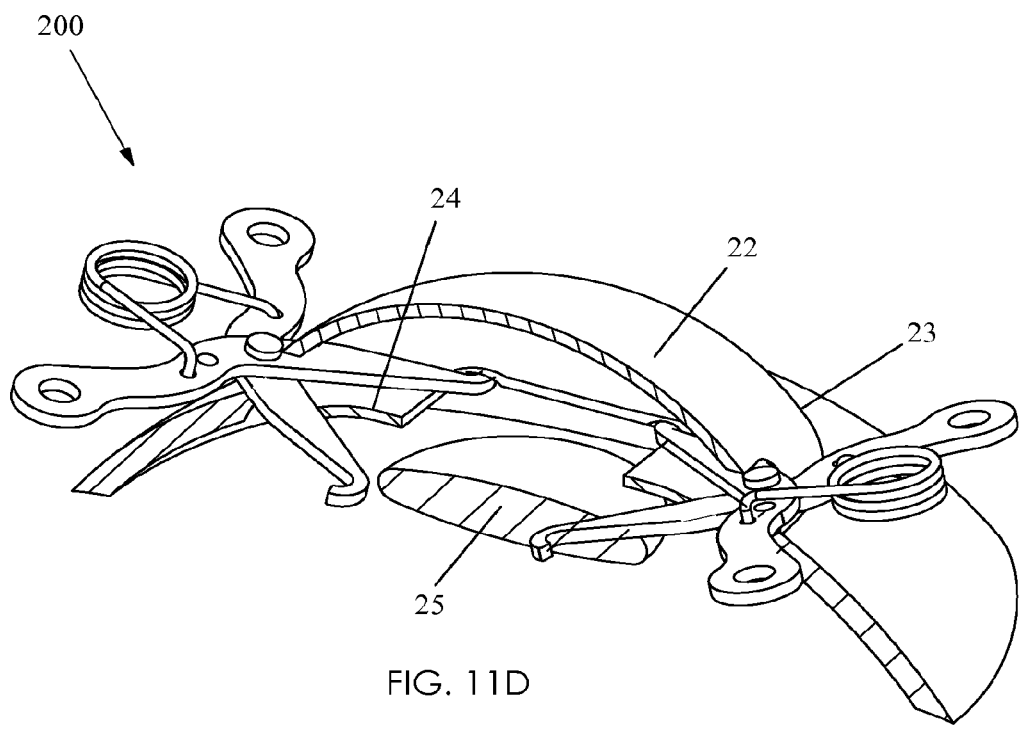

FIG. 11B illustrates iris retractor 200 in a non-expanded orientation inserted through a small incision at the limbus 23. Handles are squeezed and held together so that slender elements are retracted together, as shown in FIG. 11. FIG. 11 illustrates iris retractor 200 in an expanded orientation, wherein hooks grab and hook onto the iris 24 and retract the iris 24 for exposing the lens to provide a good working opening for the surgeon.

In another embodiment, the phrases "iris retractor" and "iris retractor assembly" are used interchangeably.

In another embodiment the maximal distance between hooks in a fully expanded retractor is 12 mm. In another embodiment the maximal distance between hooks in a fully expanded retractor is 11 mm. In another embodiment the maximal distance between hooks in a fully expanded retractor is 10 mm. In another embodiment the maximal distance between hooks in a fully expanded retractor is 9 mm. In another embodiment the maximal distance between hooks in a fully expanded retractor is 8 mm. In another embodiment the maximal distance between hooks in a fully expanded retractor is 7 mm. In another embodiment the maximal distance between hooks in a fully expanded retractor is 6.5 mm. In another embodiment the maximal distance between hooks in a fully expanded retractor is 4 to 6.5 mm.

In some embodiments, the maximal length of slender element of iris retractor is measured from protruding ear to distal tooth or. In some embodiments, the length of each one of the slender elements is 3.5 to 15 millimeters (mm). In some embodiments, the length of each one of the slender elements is 4.05 to 12.3 millimeters (mm). In some embodiments, the length of each one of the slender elements is 5.5 to 11 mm. In some embodiments, the length of each one of the slender elements is 7 to 9.5 mm. In some embodiments, the length of each one of the slender elements is 8 to 8.8 mm. In some embodiments, the length of each one of the slender elements is 8.1 to 8.3 mm.

In another embodiment, the portion of said slender element extending from the pivot to the distal end (distal tooth) is between 1.5 mm to 8 mm. In some embodiments, the length of slender element 102 of iris retractor from pivot member to distal end (such as distal tooth) is 2.55 to 7.8 mm. In some embodiments, the length of slender element of iris retractor from pivot member to distal end is 3 to 7 mm. In some embodiments, the length of slender element of iris retractor from pivot member to distal end is 3.5 to 6.5 mm. In some embodiments, the length of slender element of iris retractor 100 from pivot member to distal end is 4.3 to 5.8 mm. In some embodiments, the length of slender element of iris retractor from pivot member to distal end is 5 to 5.4 mm.

In another embodiment, the maximal length of slender element of iris retractor from pivot member to distal end is at least 30% of the entire length of the slender element. In another embodiment, the maximal length of slender element of iris retractor from pivot member to distal end is at least 35% of the entire length of the slender element. In another embodiment, the maximal length of slender element of iris retractor from pivot member to distal end is at least 40% of the entire length of the slender element. In another embodiment, the maximal length of slender element of iris retractor from pivot member to distal end is at least 45% of the entire length of the slender element. In another embodiment, the maximal length of slender element of iris retractor from pivot member to distal end is at least 50% of the entire length of the slender element. In another embodiment, the maximal length of slender element of iris retractor from pivot member to distal end is at least 55% of the entire length of the slender element. In another embodiment, the maximal length of slender element of iris retractor from pivot member to distal end is at least 60% of the entire length of the slender element. In another embodiment, the maximal length of slender element of iris retractor from pivot member to distal end is at least 65% of the entire length of the slender element. In another embodiment, the maximal length of slender element of iris retractor from pivot member to distal end is at least 70% of the entire length of the slender element.

In another embodiment, the maximal width along the portion of a slender element extending from the pivot to the distal end is 2.5 mm. and keep 1.5 mm, 1.1, 1 to preferred. In another embodiment, the maximal width along the portion of a slender element extending from the pivot to the distal end is 2 mm. In another embodiment, the maximal width along the portion of a slender element extending from the pivot to the distal end is 1.8 mm. In another embodiment, the maximal width along the portion of a slender element extending from the pivot to the distal end is 1.5 mm. In another embodiment, the maximal width along the portion of a slender element extending from the pivot to the distal end is 1.3 mm. In another embodiment, the maximal width along the portion of a slender element extending from the pivot to the distal end is 1 mm. In another embodiment, the width along the portion of a slender element extending from the pivot to the distal end is 0.5 mm to 2 mm. In another embodiment, the maximal width along the portion of a slender element extending from the pivot to the distal end is at the distal tooth (also referred to as iris grabbing hook).

In another embodiment, the grabbing hook protrudes laterally 0.25 mm to 1.2 mm from the lateral surface of a slender element at its distal end (see 188 in FIG. 14 B). In another embodiment, the grabbing hook protrudes laterally 0.4 mm to 1.0 mm from the lateral surface of a slender element at its distal end. In another embodiment, the grabbing hook protrudes laterally 0.5 mm to 0.8 mm from the lateral surface of a slender element at its distal end. In another embodiment, the grabbing hook protrudes laterally 0.5 mm to 0.7 mm from the lateral surface of a slender element at its distal end.

In some embodiments, the minimal width of a portion of slender element of iris retractor extending from pivot member to the proximal end is 0.9 mm. In some embodiments, the minimal width of a portion of slender element of iris retractor extending from pivot member to the proximal end is 0.8 mm. In some embodiments, the minimal width of a portion of slender element of iris retractor extending from pivot member to the proximal end is 0.7 mm. In some embodiments, the minimal width of a portion of slender element of iris retractor extending from pivot member to the proximal end is 0.6 mm. In some embodiments, the minimal width of a portion of slender element of iris retractor extending from pivot member to the proximal end is 0.5 mm. In some embodiments, the minimal width of a portion of slender element of iris retractor extending from pivot member to the proximal end is 0.4 mm. In some embodiments, the minimal width of a portion of slender element of iris retractor extending from pivot member to the proximal end is 0.3 mm. In some embodiments, the minimal width of a portion of slender element of iris retractor extending from pivot member to the proximal end is 0.25 mm. In some embodiments, the minimal width of a portion of slender element of iris retractor extending from pivot member to the proximal end is 0.15 mm.

In some embodiments, the distance between the inner edges of proximal teeth of iris retractor when slender element is in a maximal extended orientation, equals to 2.9 to 9.3 mm. In some embodiments, the distance between the inner edges of proximal teeth of iris retractor when slender element is in a maximal extended orientation, equals to 3.6 to 8.5 mm. In some embodiments, the distance between the inner edges of proximal teeth of iris retractor when slender element is in a maximal extended orientation, equals to 4.3 to 7.7 mm. In some embodiments, the distance between the inner edges of proximal teeth of iris retractor when slender element is in a maximal extended orientation, equals to 5.05 to 6.95 mm. In some embodiments, the distance between the inner edges of proximal teeth of iris retractor when slender element is in a maximal extended orientation, equals to 5.8 to 6.2 mm.

In some embodiments, the distance between the distal ends of each slender element of the iris retractor when the retractor is in a maximal extended orientation, equals to 2.9 to 9.3 mm. In some embodiments the distance between the distal ends of each slender element of the iris retractor when the retractor is in a maximal extended orientation, equals to 3.6 to 8.5 mm. In some embodiments, the distance between the distal ends of each slender element of the iris retractor when the retractor is in a maximal extended orientation, equals to 4.3 to 7.7 mm. In some embodiments, the distance between the distal ends of each slender element of the iris retractor when the retractor is in a maximal extended orientation, equals to 5.05 to 6.95 mm. In some embodiments, the distance between the distal ends of each slender element of the iris retractor when the retractor is in a maximal extended orientation, equals to 5.8 to 6.2 mm.

In some embodiments, the distance between the inner edges of proximal teeth of iris retractor when retractor is in a maximal contracted orientation equals to 0.07 to 0.38 mm. In some embodiments, the distance between the inner edges of proximal teeth of iris retractor when retractor is in a maximal contracted orientation equals to 0.11 to 0.34 mm. In some embodiments, the distance between the inner edges of proximal teeth of iris retractor when retractor is in a maximal contracted orientation equals to 0.14 to 0.3 mm. In some embodiments, the distance between the inner edges of proximal teeth of iris retractor when retractor is in a maximal contracted orientation equals to 0.16 to 0.27 mm. In some embodiments, the distance between the inner edges of proximal teeth of iris retractor when slender element is in a maximal contracted orientation equals to 0.18 to 0.23 mm.

In some embodiments, the distance between the proximal end and pivot member of the iris retractor when the retractor is in a maximal extended orientation, equals to 0.45 to 1.44 mm. In some embodiments, the distance between the proximal end and pivot member of the iris retractor when the retractor is in a maximal extended orientation, equals to 0.55 to 1.34 mm. In some embodiments, the distance between the proximal end and pivot member of the iris retractor when the retractor is in a maximal extended orientation, equals to 0.65 to 1.25 mm. In some embodiments, the distance between the proximal end and pivot member of the iris retractor when the retractor is in a maximal extended orientation, equals to 0.75 to 1.15 mm. In some embodiments, the distance between the proximal end and pivot member of the iris retractor when the retractor is in a maximal extended orientation, equals to 0.85 to 1.04 mm.

In some embodiments, the distance between the proximal end and pivot member of the iris retractor when the retractor is in a maximal contracted orientation/configuration, equals to 1.47 to 4.56 mm. In some embodiments, the distance between the proximal end and pivot member of the iris retractor when the retractor is in a maximal contracted orientation, equals to 1.87 to 4.15 mm. In some embodiments, the distance between the proximal end and pivot member of the iris retractor when the retractor is in a maximal contracted orientation, equals to 2.2 to 3.75 mm. In some embodiments, the distance between the proximal end and pivot member of the iris retractor when the retractor is in a maximal contracted orientation, equals to 2.6 to 3.4 mm. In some embodiments, the distance between the proximal end and pivot member of the iris retractor when the retractor is in a maximal contracted orientation, equals to 2.8 to 3.3 mm.

In some embodiments, the distance between pivot member and a distal edge of distal tooth of the iris retractor (such as in FIG. 14) equals to 1.5 to 4.74 mm when retractor is in a maximal extended orientation. In some embodiments, the distance between pivot member and a distal edge of distal tooth of the iris retractor (such as in FIG. 14) is 1.9 to 4.3 mm when retractor is in a maximal extended orientation. In some embodiments, the distance between pivot member and a distal edge of distal tooth of the iris retractor (such as in FIG. 14) is 2.3 to 3.9 mm when retractor is in a maximal extended orientation. In some embodiments, the distance between pivot member and a distal edge of distal tooth of the iris retractor (such as in FIG. 14) is 2.7 to 3.5 mm when retractor is in a maximal extended orientation. In some embodiments, the distance between pivot member and a distal edge of distal tooth of the iris retractor (such as in FIG. 14) equals to 2.85 to 3.3 mm when retractor is in a maximal extended orientation.

In some embodiments, the phrase "slender elements" means slender elements of a retractor. In some embodiments, the phrase "slender elements" is synonymous with the term "retractor".

In some embodiments, the distance between pivot member and a distal edge of distal tooth of the iris retractor (such as in FIG. 14) equals to 2.55 to 7.8 mm when retractor is in a maximal contracted orientation. In some embodiments, the distance between pivot member and a distal edge of distal tooth of the iris retractor (such as in FIG. 14) equals to 3.15 to 7.2 mm when retractor is in a maximal contracted orientation. In some embodiments, the distance between pivot member and a distal edge of distal tooth of the iris retractor (such as in FIG. 14) equals to 3.75 to 6.6 mm when retractor is in a maximal contracted orientation. In some embodiments, the distance between pivot member and a distal edge of distal tooth of the iris retractor (such as in FIG. 14) equals to 4.4 to 6 mm when retractor is in a maximal contracted orientation. In some embodiments, the distance between pivot member and a distal edge of distal tooth of the iris retractor (such as in FIG. 14) equals to equals to 4.8 to 5.4 mm when retractor is in a maximal contracted orientation.

In some embodiments, the bulge (see FIG. 14) is a lateral protrusion coupled to the ear/handle at the proximal portion or proximal end of the retractor and is used for gripping the retractor during insertion to the eye. In some embodiments, the lateral protrusion of the bulge is 0.1 to 0.5 mm. In some embodiments, the lateral protrusion of the bulge is 0.18 to 0.45 mm. In some embodiments, the lateral protrusion of the bulge is 0.23 to 0.4 mm. In some embodiments, the lateral protrusion of the bulge is 0.25 to 0.4 mm. In some embodiments, the lateral protrusion of the bulge is 0.28 to 0.33 mm.

In some embodiments, the length of the protruding ear of the handle is 0.2 to 0.9 mm. In some embodiments, the length of the protruding ear of the handle is 0.27 to 0.77 mm. In some embodiments, the length of the protruding ear of the handle is 0.32 to 0.71 mm. In some embodiments, the length of the protruding ear of the handle is 0.4 to 0.66 mm. In some embodiments, the length of the protruding ear of the handle is 0.45 to 0.58 mm.

In some embodiments, the radius of a protruding ear (see FIG. 14) is 0.5 to 1.5 mm. In some embodiments, the radius of a protruding ear (see FIG. 14) is 1.1 mm. In some embodiments, the radius of a protruding ear (see FIG. 14) is 0.8 to 1.0 mm. In some embodiments, the radius of a protruding ear (see FIG. 14) is 0.86 to 0.9 mm.

In some embodiments, the depth or thickness of two slender elements equals to 0.4 to 1.8 mm. In some embodiments, the depth or thickness of two slender elements equals to 0.6 to 1.5 mm. In some embodiments, the depth or thickness of two slender elements equals to 0.75 to 1.35 mm. In some embodiments, the depth or thickness of two slender elements equals to 0.85 to 1.2 mm. In some embodiments, the depth or thickness of two slender elements equals to 0.95 to 1.05 mm.

In some embodiments, the depth or thickness of a middle portion of two slender elements of the retractor equals to 0.2 to 1.2 mm. In some embodiments, the depth or thickness of a middle portion of two slender elements of the retractor equals to 0.36 to 0.92 mm. In some embodiments, the depth or thickness of a middle portion of two slender elements of the retractor equals to 0.46 to 0.82 mm. In some embodiments, the depth or thickness of a middle portion of two slender elements of the retractor equals to 0.5 to 0.75 mm. In some embodiments, the depth or thickness of a middle portion of two slender elements of the retractor equals to 0.58 to 0.65 mm.

In some embodiments, In some embodiments, the depth or thickness of the upper (proximal) portion of the slender element (i.e., as held by a medical professional with respect to a treated iris) of two slender elements of the retractor equals to 0.14 to 0.48 mm. In some embodiments, In some embodiments, the depth or thickness of the upper (proximal) portion of the slender element (i.e., as held by a medical professional with respect to a treated iris) of two slender elements of the retractor equals to 0.17 to 0.45 mm. In some embodiments, In some embodiments, the depth or thickness of the upper (proximal) portion of the slender element (i.e., as held by a medical professional with respect to a treated iris) of two slender elements of the retractor equals to 0.2 to 0.42 mm. In some embodiments, In some embodiments, the depth or thickness of the upper (proximal) portion of the slender element (i.e., as held by a medical professional with respect to a treated iris) of two slender elements of the retractor equals to 0.23 to 0.38 mm. In some embodiments, In some embodiments, the depth or thickness of the upper (proximal) portion of the slender element (i.e., as held by a medical professional with respect to a treated iris) of two slender elements of the retractor equals to 0.25 to 0.32 mm.

In some embodiments, (such as FIG. 14B) the distance (181) between the protruding ears of a fully expanded retractor is 4-14 mm. In some embodiments, (such as FIG. 14B) the distance (181) between the protruding ears of a fully expanded retractor is 4-10 mm. In some embodiments, (such as FIG. 14B) the distance (181) between the protruding ears of a fully expanded retractor is 5-8 mm. In some embodiments, (such as FIG. 14B) the distance (181) between the protruding ears of a fully expanded retractor is 6-7 mm. In some embodiments, (such as FIG. 14B) the maximal distance (190) between the distal teeth of a fully expanded retractor is 5-14 mm. In some embodiments, (such as FIG. 14B) the maximal distance (190) between the distal teeth of a fully expanded retractor is 6-12 mm. In some embodiments, (such as FIG. 14B) the maximal distance (190) between the distal teeth of a fully expanded retractor is 7-10 mm. In some embodiments, (such as FIG. 14B) the maximal distance (190) between the distal teeth of a fully expanded retractor is 8-10 mm.

In some embodiments, (such as FIG. 14B) the maximal width of the retractor at the slender elements joining spot ("the neck") such as the pivot (191) is 0.4-1.4 mm. In some embodiments, (such as FIG. 14B) the maximal width of the retractor at the slenders joining spot such as the pivot (191) is 0.5-1.2 mm. In some embodiments, (such as FIG. 14B) the maximal width of the retractor at the slenders joining spot such as the pivot (191) is 0.7-0.9 mm.

In some embodiments, (such as FIG. 14 (188), FIGS. 9-11) the maximal lateral protrusion of the hook or a portion thereof such as a tooth is 0.9 mm. In some embodiments, (such as FIG. 14, FIGS. 9-11) the maximal lateral protrusion of the hook or a portion thereof such as a tooth is 0.8 mm. In some embodiments, (such as FIG. 14, FIGS. 9-11) the maximal lateral protrusion of the hook or a portion thereof such as a tooth is 0.7 mm. In some embodiments, (such as FIG. 14 (188), FIGS. 9-11) the lateral protrusion of the hook or a portion thereof such as a tooth is 0.3-0.9 mm. In some embodiments, (such as FIG. 14 (188), FIGS. 9-11) the lateral protrusion of the hook or a portion thereof such as a tooth is 0.5-0.8 mm.

Figure 13B:
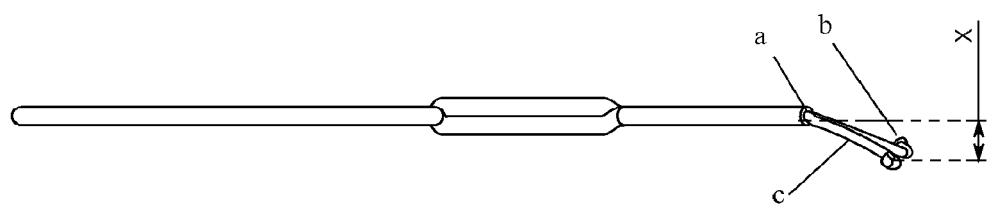

In some embodiments, the maximal diameter of a hook or the maximal width of a niche bordered by teeth 703 and 704 of a hook (such as in FIGS. 13 and 14 (185)) is 0.2-0.9 mm. In some embodiments, the maximal diameter of a hook or the maximal width of a niche bordered by teeth 703 and 704 of a hook (such as in FIGS. 13 and 14 (185)) is 0.3-0.8 mm. In some embodiments, the maximal diameter of a hook or the maximal width of a niche bordered by teeth 703 and 704 of a hook (such as in FIGS. 13 and 14 (185)) is 0.4-0.6 mm.

In some embodiments, the distance between two proximal teeth of the fully expanded retractor of FIG. 14 (distance 189) is 4-12 mm. In some embodiments, the distance between two proximal teeth of the fully expanded retractor of FIG. 14 (distance 189) is 4-8 mm. In some embodiments, the distance between two proximal teeth of the fully expanded retractor of FIG. 14 (distance 189) is 5-7 mm.

In some embodiments, the maximal distance between the proximal end to the distal end of a fully expanded retractor of the invention (such as element 182 in FIG. 14) is 4-10 mm. In some embodiments, the maximal distance between the proximal end to the distal end of a fully expanded retractor of the invention (such as element 182 in FIG. 14) is 4-8 mm. In some embodiments, the maximal distance between the proximal end to the distal end of a fully expanded retractor of the invention (such as element 182 in FIG. 14) is 4-7 mm. In some embodiments, the maximal distance between the proximal end to the distal end of a fully expanded retractor of the invention (such as element 182 in FIG. 14) is 5-6 mm.

In some embodiments, the length of the proximal portion of the fully extended retractor (extending from the pivot to the proximal end, such as distance 183 in FIG. 14) is 1-6 mm. In some embodiments, the length of the proximal portion of the fully extended retractor (extending from the pivot to the proximal end, such as distance 183 in FIG. 14) is 1-4.5 mm. In some embodiments, the length of the proximal portion of the fully extended retractor (extending from the pivot to the proximal end, such as distance 183 in FIG. 14) is 2-4 mm. In some embodiments, the length of the proximal portion of the fully extended retractor (extending from the pivot to the proximal end, such as distance 183 in FIG. 14) is 2-3.5 mm.

In some embodiments, the length of the distal portion of the fully extended retractor (extending from the pivot to the distal end, such as distance 184 in FIG. 14) is 1.5-6.5 mm. In some embodiments, the length of the distal portion of the fully extended retractor (extending from the pivot to the distal end, such as distance 184 in FIG. 14) is 1.5-5.5 mm. In some embodiments, the length of the distal portion of the fully extended retractor (extending from the pivot to the distal end, such as distance 184 in FIG. 14) is 2-5 mm. In some embodiments, the length of the distal portion of the fully extended retractor (extending from the pivot to the distal end, such as distance 184 in FIG. 14) is 25-4 mm.

Figure 14A:
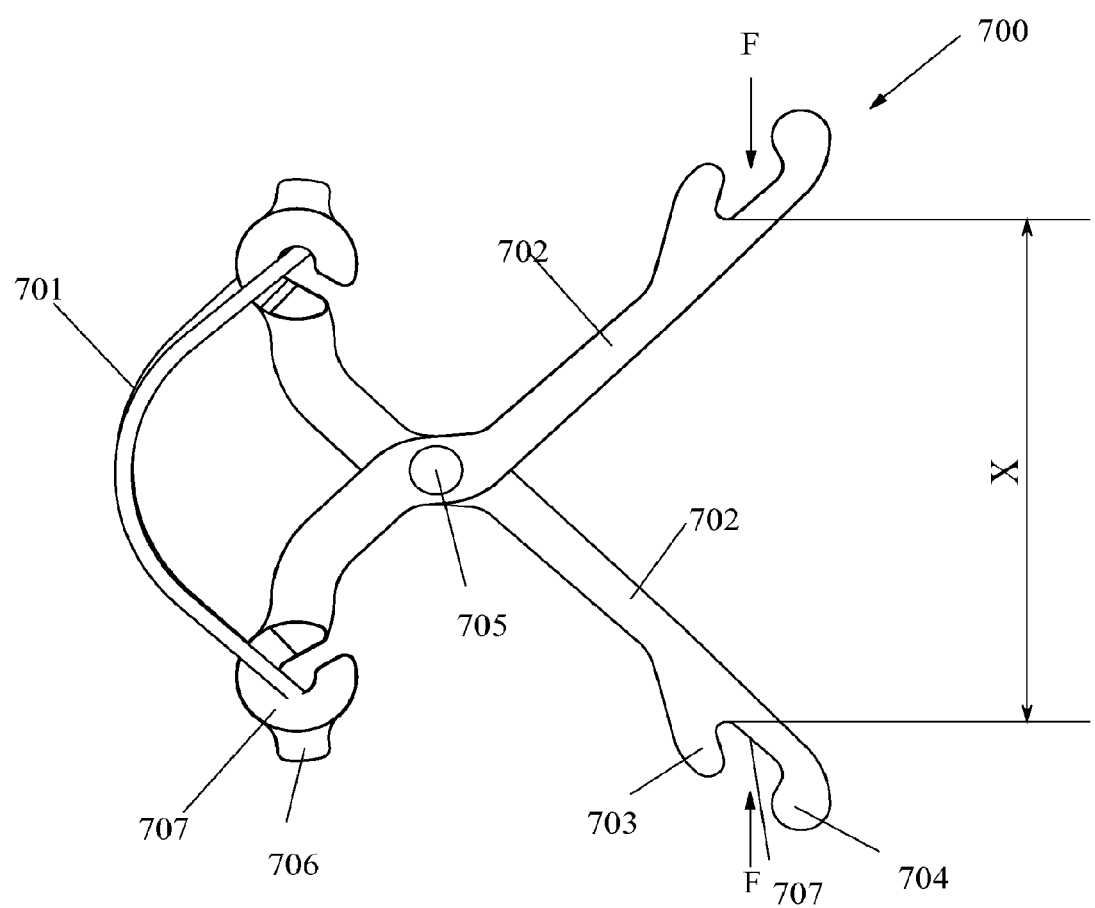
FIGS. 14A-14D are simplified pictorial illustrations of an iris retractor, constructed and operative in accordance with another embodiment of the present invention.
Figure 14B:
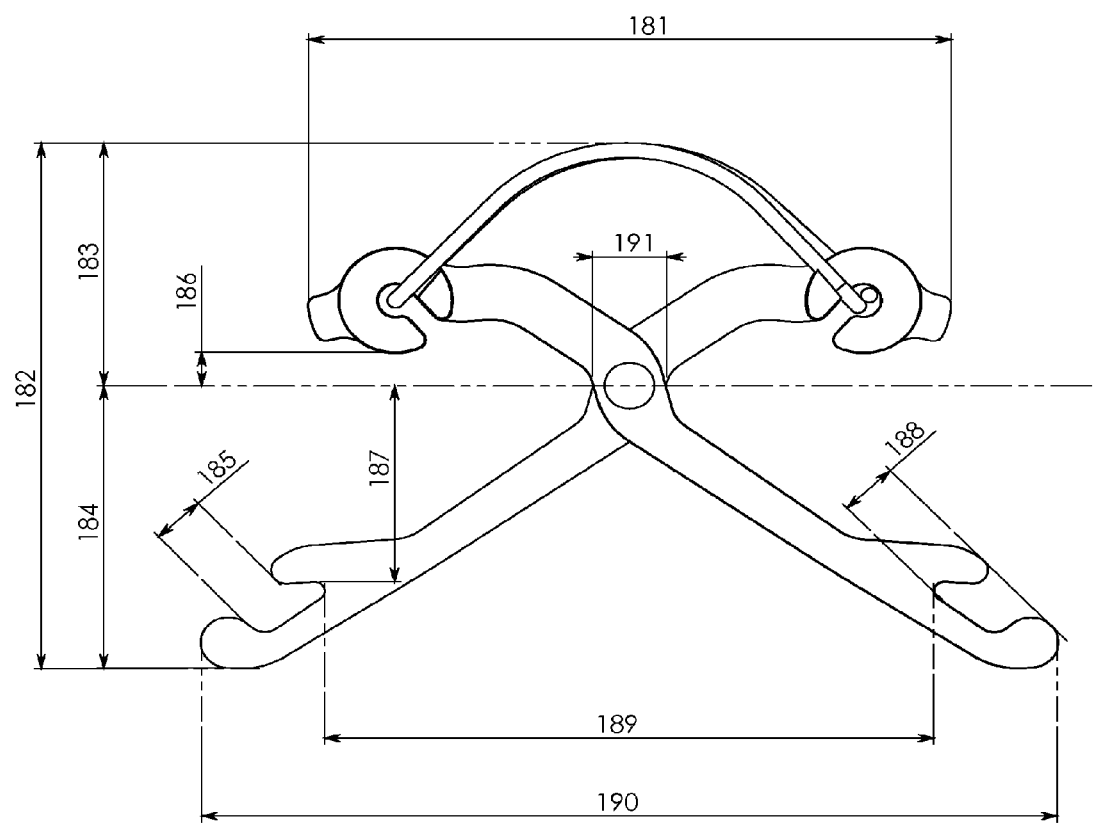
Figure 14C:
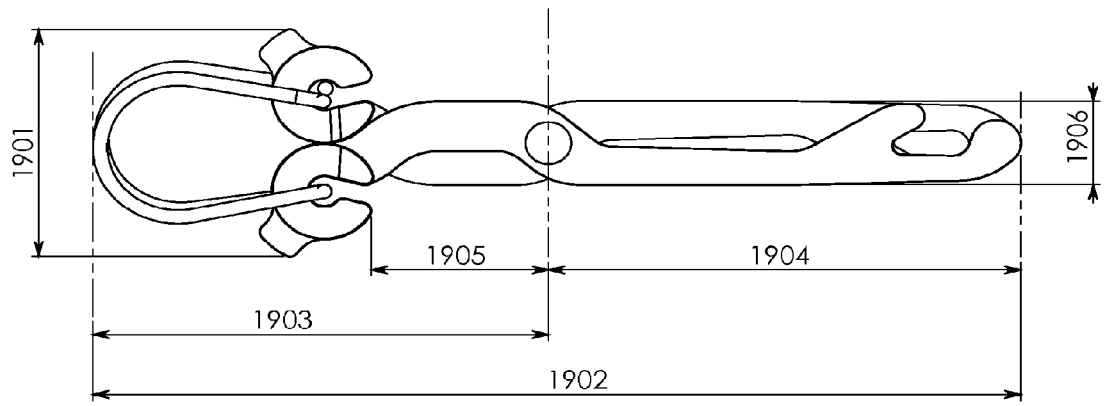
Figure 14D:
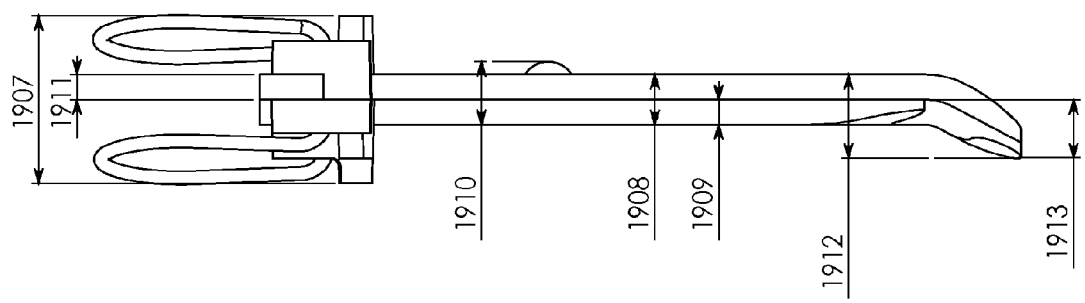

In some embodiments, such as in FIG. 14 or 14D a fully retracted or closed retractor of the invention has a maximal width of 5 mm (element 1901 in FIG. 14C). In some embodiments, such as in FIG. 14 or 14D a fully retracted or closed retractor of the invention has a maximal width of 4.5 mm (element 1901 in FIG. 14C). In some embodiments, such as in FIG. 14 or 14D a fully retracted or closed retractor of the invention has a maximal width of 4 mm (element 1901 in FIG. 14C). In some embodiments, such as in FIG. 14 or 14D a fully retracted or closed retractor of the invention has a maximal width of 3 mm (element 1901 in FIG. 14C). In some embodiments, such as in FIG. 14 or 14D a fully retracted or closed retractor of the invention has a width of between 1.2 to 5 mm (element 1901 in FIG. 14C). In some embodiments, such as in FIG. 14 or 14D a fully retracted or closed retractor of the invention has a width of between 1.8 to 4 mm (element 1901 in FIG. 14C). In some embodiments, such as in FIG. 14 or 14D a fully retracted or closed retractor of the invention has a width of between 2 to 3.5 mm (element 1901 in FIG. 14C).

In some embodiments, the length of the proximal portion of the fully retracted or closed retractor (extending from the pivot to the proximal end, such as distance 1903 in FIG. 14C) is 2-10 mm. In some embodiments, the length of the proximal portion of the fully retracted or closed retractor (extending from the pivot to the proximal end, such as distance 1903 in FIG. 14C) is 3-8 mm. In some embodiments, the length of the proximal portion of the fully retracted or closed retractor (extending from the pivot to the proximal end, such as distance 1903 in FIG. 14C) is 3.5-7 mm. In some embodiments, the length of the proximal portion of the fully retracted or closed retractor (extending from the pivot to the proximal end, such as distance 1903 in FIG. 14C) is 3.5-5.5 mm.

In some embodiments, the maximal distance between the proximal end to the distal end of a fully retracted or closed retractor of the invention (such as element 1902 in FIG. 14C) is 5-18 mm. In some embodiments, the maximal distance between the proximal end to the distal end of a fully retracted or closed retractor of the invention (such as element 1902 in FIG. 14C) is 5-15 mm. In some embodiments, the maximal distance between the proximal end to the distal end of a fully retracted or closed retractor of the invention (such as element 1902 in FIG. 14C) is 7-15 mm. In some embodiments, the maximal distance between the proximal end to the distal end of a fully retracted or closed retractor of the invention (such as element 1902 in FIG. 14C) is 8-12 mm.

In some embodiments, the length of the distal portion of the fully retracted or closed retractor (extending from the pivot to the distal end, such as distance 1904 in FIG. 14C) is 2.5-9.5 mm. In some embodiments, the length of the distal portion of the fully retracted or closed retractor (extending from the pivot to the distal end, such as distance 1904 in FIG. 14C) is 3.5-8.5 mm. In some embodiments, the length of the distal portion of the fully retracted or closed retractor (extending from the pivot to the distal end, such as distance 1904 in FIG. 14C) is 4-7 mm. In some embodiments, the length of the distal portion of the fully retracted or closed retractor (extending from the pivot to the distal end, such as distance 1904 in FIG. 14C) is 4.5-5.5 mm.

In some embodiments, the maximal width of the distal portion (extending from the pivot to the distal end) of a fully retracted or closed retractor (such as in FIG. 14C) is 4 mm. In some embodiments, the maximal width of the distal portion (extending from the pivot to the distal end) of a fully retracted or closed retractor is 3 mm. In some embodiments, the maximal width of the distal portion (extending from the pivot to the distal end) of a fully retracted or closed retractor is 2 mm. In some embodiments, the maximal width of the distal portion (extending from the pivot to the distal end) of a fully retracted or closed retractor is 1.5 mm. In some embodiments, the width of the distal portion (extending from the pivot to the distal end) of a fully retracted or closed retractor is 0.3-4 mm. In some embodiments, the width of the distal portion (extending from the pivot to the distal end) of a fully retracted or closed retractor is 0.5-2.5 mm. In some embodiments, the width of the distal portion (extending from the pivot to the distal end) of a fully retracted or closed retractor is 0.5-1.5 mm.

In some embodiments, the maximal thickness of a fully retracted or closed retractor of the invention (such as element 1907 in FIG. 14D) is 6 mm. In some embodiments, the thickness of a fully retracted or closed retractor of the invention (such as element 1907 in FIG. 14D) is 4 mm. In some embodiments, the thickness of a fully retracted or closed retractor of the invention (such as element 1907 in FIG. 14D) is 3 mm. In some embodiments, the thickness of a fully retracted or closed retractor of the invention (such as element 1907 in FIG. 14D) is 2.5 mm. In some embodiments, the thickness of the proximal end of a fully retracted or closed retractor of the invention (such as element 1907 in FIG. 14D) is 1-3 mm. In some embodiments, the thickness of a fully retracted or closed retractor of the invention (such as element 1907 in FIG. 14D) is 0.3-3 mm. In some embodiments, the thickness of a fully retracted or closed retractor of the invention (such as element 1907 in FIG. 14D) is 0.3-2.5 mm.

In some embodiments, the thickness of a each of the slender elements (such as element 1911 in FIG. 14D) is 0.1-1.4 mm. In some embodiments, the thickness of a each of the slender elements (such as element 1911 in FIG. 14D) is 0.1-0.8 mm. In some embodiments, the thickness of a each of the slender elements (such as element 1911 in FIG. 14D) is 0.1-0.6 mm.

In some embodiments, devices of the invention (such as in FIG. 14A) were made with a spring having differential force (F) along the expansion plane (in grams) according to the measures provided in table 1:

TABLE 1

| Expander Spring force F [gr] | Distance between hooks (iris opening) x [mm] |
| --- | --- |
| 2-6 | 5.7 |
| 4-8 | 5.3 |
| 4-8 | 4.9 |
| 5-9 | 4.5 |
| 6-10 | 4.1 |
| 7-11 | 3.7 |
| 8-12 | 3.3 |
| 9-13 | 2.9 |

It will be appreciated by persons skilled in the art that the present invention is not limited by what has been particularly shown and described hereinabove. Rather the scope of the present invention includes both combinations and sub-combinations of the features described hereinabove as well as modifications and variations thereof which would occur to a person of skill in the art upon reading the foregoing description and which are not in the prior art.

What is claimed is:

1. A method for iris retraction, comprising:
   (a) providing an iris retractor that comprises:
      a first slender element and a second slender element, each slender element comprising: a proximal handle and a distal grabbing hook having a concave side, and a proximal handle, and
      a joining mechanism operatively coupling the first and second slender elements, and being configured to endow said iris retractor with at least two configurations: a retracted configuration and an expanded configuration, wherein, in the retracted configuration, said concave sides of said distal grabbing hooks face one another, and wherein, in the expanded configuration, said concave sides of said distal grabbing hooks face away from one another;
   (b) inserting the first and second slender elements through an incision at or near the limbus of an eye, when the iris retractor is in the retracted configuration; and
   (c) manipulating the proximal handles to transform the iris retractor from the retracted configuration to the expanded configuration, while grasping and retracting the iris of the eye with the distal grabbing hooks.

2. The method according to claim 1, wherein the incision is 1.0-1.5 millimeters long.

3. The method according to claim 1, wherein:
   the iris retractor is normally expanded;
   the method further comprises, during the insertion of the first and second slender elements through the incision, holding the first and second slender elements by squeezing their respective proximal handles, to maintain the iris retractor in the retracted configuration; and
   the manipulating of the proximal handles comprises ceasing to squeeze the proximal handles.

4. The method according to claim 3, wherein the proximal handles are spring-loaded.

5. The method according to claim 4, wherein the joining mechanism comprises a pivot.

6. The method according to claim 1, further comprising, after step (c), removing the lens of the eye.

7. The method according to claim 6, wherein the removing of the lens is by phacoemulsification.

8. The method according to claim 6, further comprising, following the removal of the lens, manipulating the proximal handles to transform the iris retractor from the expanded configuration to the retracted configuration, and withdrawing the first and second slender elements from the eye, through the incision.

* * * * *